(12) United States Patent
Ewing et al.

(10) Patent No.: US 8,143,425 B2
(45) Date of Patent: Mar. 27, 2012

(54) HETEROCYCLIC AROMATIC COMPOUNDS USEFUL AS GROWTH HORMONE SECRETAGOGUES

(75) Inventors: William R. Ewing, Yardley, PA (US); Jun Li, Princeton, NJ (US); Richard B. Sulsky, West Trenton, NJ (US); Andres S. Hernandez, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 669 days.

(21) Appl. No.: 11/247,491

(22) Filed: Oct. 11, 2005

(65) Prior Publication Data

US 2006/0079562 A1    Apr. 13, 2006

Related U.S. Application Data

(60) Provisional application No. 60/617,790, filed on Oct. 12, 2004.

(51) Int. Cl.
*A61K 31/415* (2006.01)
*C07D 231/12* (2006.01)

(52) U.S. Cl. ..................... 548/375.1; 514/406
(58) Field of Classification Search ................ 548/375.1
See application file for complete search history.

(56) References Cited

U.S. PATENT DOCUMENTS

| | | | |
|---|---|---|---|
| 3,239,345 | A | 3/1966 | Hodge et al. |
| 3,666,756 | A | 5/1972 | Fukumura et al. |
| 4,036,979 | A | 7/1977 | Asato |
| 4,411,890 | A | 10/1983 | Momany |
| 5,179,080 | A | 1/1993 | Rothkopf |
| 5,612,359 | A | 3/1997 | Murugesan |
| 6,043,265 | A | 3/2000 | Murugesan et al. |
| 6,184,231 | B1 | 2/2001 | Hewawasam et al. |
| 6,525,059 | B1 * | 2/2003 | Anantanarayan et al. .... 514/256 |
| 6,548,529 | B1 | 4/2003 | Robl et al. |
| 6,979,686 | B1 * | 12/2005 | Naraian et al. ............. 514/235.8 |
| 7,453,002 | B2 * | 11/2008 | Hangeland et al. ........ 548/311.7 |
| 2004/0072881 | A1 | 4/2004 | Robl et al. |
| 2007/0037857 | A1 | 2/2007 | Perrissoud et al. |

FOREIGN PATENT DOCUMENTS

| | | |
|---|---|---|
| WO | WO 89/07110 | 8/1989 |
| WO | WO 89/07111 | 8/1989 |
| WO | WO 00/01389 | 1/2000 |
| WO | WO 00/54729 | 9/2000 |
| WO | WO 2004/021984 | 3/2004 |

OTHER PUBLICATIONS

Ankersen, M. et al., "Growth hormone secretagogues: recent advances and applications", DDT, vol. 4(11), pp. 497-506 (1999).
Edwards, J. et al., "Nonsteroidal Androgen Receptor Agonists Based on 4-(Trifluoromethyl)-2H-Pyrano[3,2-g]Quinolin-2-One", Bioorganic & Medical Chemistry Letters, vol. 9, pp. 1003-1008 (1999).
Hamann. L. et al., "Discovery of a Potent, Orally Active, Nonsteroidal Androgen receptor Agonist: 4-Ethyl-1,2,3,4-tetrahydro-6-(trifluoromethyl)-8-pyridono[5,6-9]quinoline (LG121071)", J. Med. Chem., vol. 42, pp. 210-212 (1999).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure*", Journal of Clinical Endocrinology and Metabolism, vol. 82(3), pp. 727-734 (1997).
Jones, R. et al., "A Second-Generation Cycloaddition Route to 5-Substituted 3-Acyltetramic Acids", Synlett, vol. S1, pp. 873-876 (1999).
Konradi, A. et al., "Pinacol Cross Coupling of 2[N-(Alkoxycarbonyl)amino] Aldehydes and Aliphatic Aldehydes by $[V_2Cl_3(THF)_6]_2[Zn_2Cl_6]$. Synthesis of *syn*, *syn*-3-[N-(Alkoxycarbonyl)amino] 1,2-Diols", J. Am. Chem. Soc., vol. 116, pp. 1316-1323 (1994).
Quintela, J. et al., "A Novel Synthesis of Dihydropyrimidothienopyriadazine Derivatives", Tetrahedron, vol. 54, pp. 8107-8122 (1998).
Svensson, J. et al., "Growth hormone secretagogues", Expert Opinion on Therapeutic Patents, vol. 10(7), pp. 1071-1080 (2000).

* cited by examiner

*Primary Examiner* — Laura L. Stockton
(74) *Attorney, Agent, or Firm* — Terence J. Bogie

(57) ABSTRACT

Novel heterocyclic aromatic compounds are provided that are useful in stimulating endogenous production or release of growth hormone, said compounds having the general structure of formula I

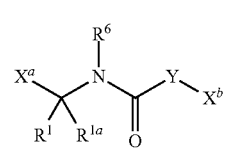

wherein $R^1$, $R^{1a}$, $R^6$, $X^a$, $X^b$ and Y are as described herein.
The compounds provided herein are useful in treating obesity, osteoporosis (improving bone density) and in improving muscle mass and muscle strength.

11 Claims, No Drawings

HETEROCYCLIC AROMATIC COMPOUNDS USEFUL AS GROWTH HORMONE SECRETAGOGUES

RELATED APPLICATIONS

This application claims priority benefit under title 35 §119 (E) of U.S. Provisional Application No. 60/617,790, filed Oct. 12, 2004, the contents of which are herein incorporated by reference.

BACKGROUND OF THE INVENTION

Growth hormone is important not only for linear body growth, but is also important for the maintenance of body composition, metabolism and heart function in adult life. In fact, treatment with growth hormone is employed in both adults and children suffering from growth hormone deficiency. Treatment with growth hormone has been shown to reduce body fat, increase fat-free mass, increase muscle strength, improve bone mass and well-being. These beneficial effects associated with growth hormone treatment suggest that growth hormone treatment may further be useful for the treatment of osteoporosis, frailty in the elderly, complicated fracture, cardiomyopathy, obesity and some nitrogen-wasting conditions resulting from, for example, AIDS, chronic dialysis, catabolic disease and glucocorticoid treatment. Johan Svensson, *Exp. Opin. Ther. Patents*, 2000 10(7) 1071-1080; Ankersen et al., *DDT*, 1999, 4(11) 497-506. Moreover, growth hormone therapy is also been explored with a view towards reversing changes associated with aging.

Current methods for administering growth hormone are invasive in that synthetic growth hormone must be administered by daily injection. Therefore, if an orally administered secretagogue could be introduced that is safe, efficacious, well tolerated, it would provide an attractive treatment alternative to current growth hormone treatment.

Growth hormone secretagogues are synthetically produced peptides and non-peptides that stimulate the endogenous production and/or release of growth hormone by acting on one or more specific receptors at both pituitary and hypothalamic levels. Accordingly, orally active growth hormone secretagogues could offer attractive alternatives to traditional growth hormone therapy, thus providing a more convenient means to treat a wider array of diseases or disorders associated with growth hormone levels in patient circulation.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents.

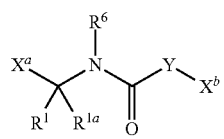

I including all pharmaceutically acceptable salts and stereoisomers, wherein:

$R^1$ and $R^{1a}$ are independently selected from the group consisting of hydrogen, alkyl, aryl, alkenyl, alkynyl, arylalkyl, cycloalkyl, cycloalkylalkyl, alkoxyalkyl, arylalkyloxyalkyl, aryloxyalkyl, heteroaryl, cycloalkylalkoxyalkyl, heteroarylalkyl, cycloheteroalkyl and cycloheteroalkylalkyl, wherein the alkyl, aryl, alkenyl, alkynyl, arylalkyl, cycloalkyl, cycloalkylalkyl, alkoxyalkyl, arylalkyloxyalkyl, aryloxyalkyl, heteroaryl, cycloalkylalkoxyalkyl, heteroarylalkyl, cycloheteroalkyl and cycloheteroalkylalkyl may be optionally substituted by 1,2 or 3-substituents selected from the group consisting of halogen, $-OR^8$, $-OC(O)R^8$, alkyl, phenyl, phenoxy, halophenyl, $-CF_3$, $-OCF_3$, $-N(R^{8a})C(O)(R^8)$ and $-N(R^8)(R^{8a})$;

$X^a$ is selected from the group consisting of

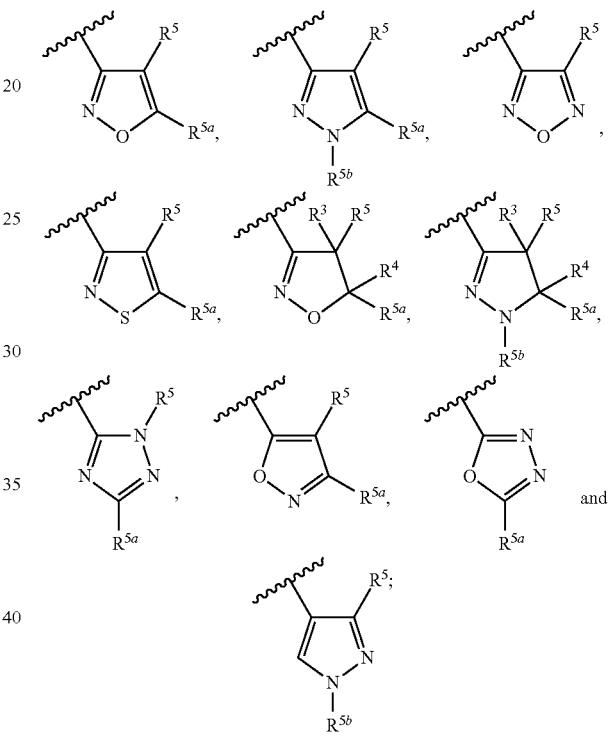

$R^5$ and $R^{5a}$ are independently selected from the group consisting of hydrogen, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, cycloalkylalkoxyalkyl, $-SO_2T^1$, $-SO_2N(T^{1a})T^1$, $-N(T^{1a})T^1$, heteroarylalkyl, halo, alkylamino, cycloalkylamino and $J^1$, wherein alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, heteroaryloxyalkyl, cycloalkylalkoxyalkyl, or heteroarylalkyl may optionally be substituted with 1 to 3 $J^1$;

$R^{5b}$ is selected from the group consisting of hydrogen, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, cycloalkylalkoxyalkyl, heteroarylalkyl, $-SO_2T^1$, $-SO_2N(T^{1a})T^1$ and $J^1$, wherein alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl, heteroaryloxyalkyl, cycloalkylalkoxyalkyl, or heteroarylalkyl may optionally be substituted with 1 to 3 $J^1$;

$R^3$ is selected from the group consisting of hydrogen, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl and cycloalkylalkoxyalkyl, wherein $R^3$ and $R^5$ taken together may form a spiro ring;

$R^4$ is selected from the group consisting of hydrogen, alkyl, aryl, alkenyl, arylalkenyl, alkynyl, arylalkyl, arylalkynyl, cycloalkylalkyl, alkoxyalkyl, aryloxyalkyl, arylalkyloxyalkyl, heteroaryl and cycloalkylalkoxyalkyl, wherein $R^4$ and $R^{5a}$ taken together may form a spiro ring;

$J^1$ is selected from the group consisting of nitro, $-(CH_2)_v N(T^{1a})C(O)T^1$, $-(CH_2)_v CN$, $-(CH_2)_v N(T^{1a})C(O)OT^1$, $-(CH_2)_v N(T^{1a})C(O)N(T^{1b})T^1$, $-(CH_2)_v N(T^{1a})SO_2T^1$, $-(CH_2)_v C(O)N(T^{1a})T^1$, $-(CH_2)_v C(O)OT^1$, $-(CH_2)_v OC(O)OT^1$, $-(CH_2)_v OC(O)T^1$, $-(CH_2)_v OC(O)N(T^{1a})T^1$, $-(CH_2)_v N(T^{1a})SO_2N(T^{1a})T^1$, $-(CH_2)_v OT^1$, $-(CH_2)_v SO_2T^1$, $-(CH_2)_v SO_2N(T^{1a})T^1$, $-(CH_2)_v C(O)T^1$, $-(CH_2)_v CH(OH)T^1$, $-(CH_2)_v CHN(T^{1a})T^1$, cycloheteroalkyl and heteroaryl;

$T^1$, $T^{1a}$ and $T^{1b}$ are independently selected from the group consisting of hydrogen, alkyl, alkenyl, alkynyl, lower alkylthioalkyl, alkoxyalkyl, aryl, arylalkyl, heteroaryl, heteroarylalkyl, cycloheteroalkyl and cycloalkyl, wherein alkyl, alkenyl, alkynyl, lower alkylthioalkyl, alkoxyalkyl, aryl, arylalkyl, heteroaryl, heteroarylalkyl, cycloheteroalkyl and cycloalkyl of which may optionally be substituted with 0-3 substituents selected from the group consisting of halogen, hydroxyl, $-NR^{8f}C(O)NR^{8g}R^{8i}$, $-C(O)NR^{8f}R^{8g}$, $-NR^{8f}C(O)R^{8g}$, $-CN$, $-N(R^{8f})SO_2R^{8g}$, $-OC(O)R^{8f}$, $-SO_2NR^{8f}R^{8g}$, $-SOR^{8h}$, $-SO_2R^{8j}$, alkoxy, $-COOH$, cycloheteroalkyl and $-C(O)OR^{8k}$, wherein $T^1$ and $T^{1a}$ or $T^1$ and $T^{1b}$ taken together may form a 3-8 membered heteroaryl or heterocyclo ring;

Y is selected from the group consisting of

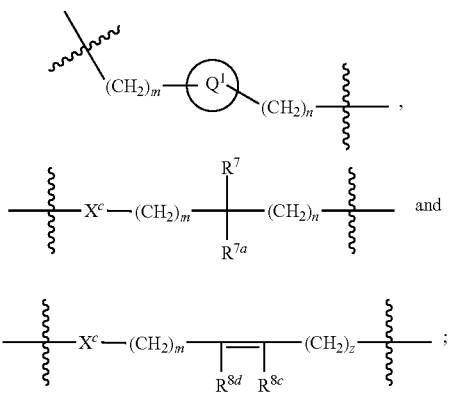

$X^c$ is selected from the group consisting of a direct bond, $-NR^{6a}$ and $-O-$;

Q is selected from the group consisting of carbon and nitrogen;

$Q^1$ is selected from the group consisting of cycloalkyl, heterocyclo, aryl and heteroaryl;

$R^7$ and $R^{7a}$ are independently selected from the group consisting of H, alkyl, $-CF_3$, phenyl, aryl, arylalkyl, and cycloalkyl, wherein one or both of $R^7$ and $R^{7a}$ independently taken together with one or both of $R^9$ and $R^{10}$ may form an alkylene bridge of 1 to 5 carbon atoms; or $R^7$ and $R^{7a}$ taken together may form a 3-7 membered ring;

$R^6$, $R^{6a}$, $R^{6b}$, $R^8$, $R^{8a}$, $R^{8d}$, $R^{8e}$, $R^{8h}$, $R^{8j}$ and $R^{8k}$ are independently selected from the group consisting of hydrogen, alkyl, alkenyl, cycloalkyl and aryl;

$X^b$ is $-NR^9R^{10}$;

$R^9$ and $R^{10}$ are independently selected from the group consisting of hydrogen and alkyl, wherein the alkyl may optionally be substituted with 1 to 3 substitutents selected from the group consisting of hydroxyl, $C_1$-$C_{10}$-alkanoyloxy, $C_1$-$C_6$ alkoxy, phenyl, phenoxy, $C_1$-$C_6$ alkoxycarbonyl, wherein $R^9$ and $R^{10}$ taken together may form $-(CH_2)_t X^d (CH_2)_u-$, $-O-$, or $-N(R^{6b})-$;

$X^d$ is $C(R^{8h})(R^{8j})$;

m and n are independently 0 to 3;

t and u are independently 1 to 3;

v is 0 to 5; and z is 1 to 3.

In an embodiment, the present application describes compounds according to Formula I wherein:

Y is

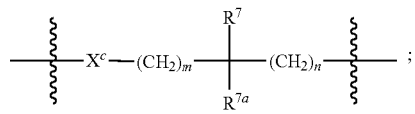

$X^c$ is a direct bond;

$R^7$ and $R^{7a}$ are alkyl;

$R^9$ and $R^{10}$ are hydrogen; and m and n are 0.

In an embodiment, the present application describes compounds according to Formula I wherein:

$R^1$ is alkyl; and $R^{1a}$ is hydrogen.

In an embodiment, the present application describes compounds according to Formula I wherein $R^6$ is hydrogen.

In an embodiment, the present application describes compounds according to Formula I wherein:

$X^a$ is selected from the group consisting of

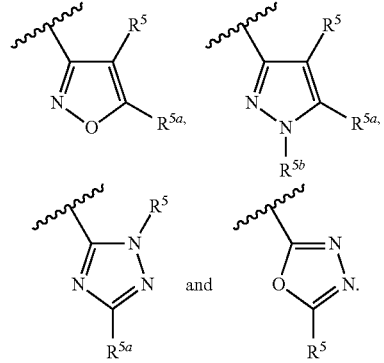

DEFINITIONS

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents including alkyl, aryl, alkenyl, alkynyl, hydroxyl, arylalkyl, cycloalkyl, cycloalkylalkyl, alkoxy, arylalkyloxy, alkanoyl, amino, haloaryl, $CF_3$, $OCF_3$, aryloxy, heteroaryl, cycloalkylalkoxyalkyl, or cycloheteroalkyl.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 7 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

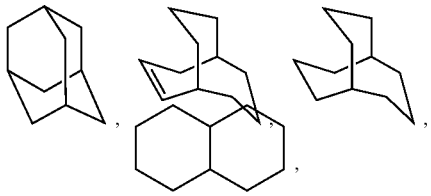

any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or preferably any of the aryl substituents as set out above.

Preferred aryl groups include substituted or un-substituted phenyl, biphenyl or naphthyl.

The term "aralkyl", "aryl-alkyl" or "aryl lower alkyl" as used herein alone or as part of another group refers to alkyl groups as discussed above having an aryl substituent, such as benzyl or phenethyl, or naphthylpropyl, or an aryl as defined above.

The term "lower alkoxyl", "alkoxyl", "aryloxyl" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 2 to 6 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the substituents for alkyl as set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the substituents for alkyl as set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Examples of $(CH_2)x$, $(CH_2)y$, $(CH_2)w$, $(CH_2)v$, $(CH_2)s$, $(CH_2)t$, $(CH_2)u$ or $(CH_2)z$ groups (which may include alkylene, alkenylene or alkynylene groups as defined herein, and may optionally include 1, 2, or 3 substituents which may be any of the alkyl substituents set out herein), are as follows:

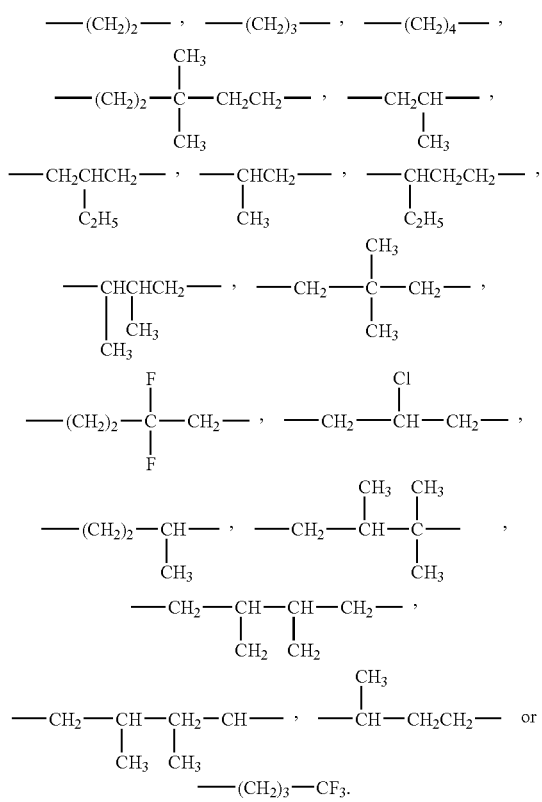

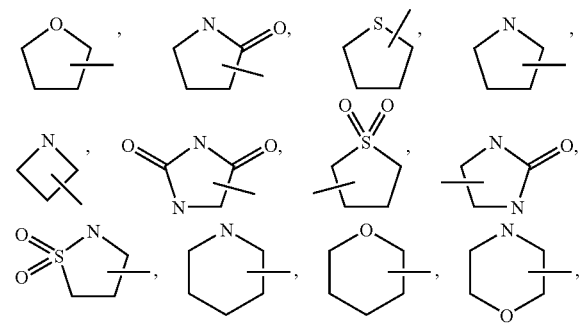

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclic", "heterocyclo" or "heterocycle" as employed herein alone or as part of another group refers to "heteroaryl" groups or "cycloheteroalkyl" groups.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

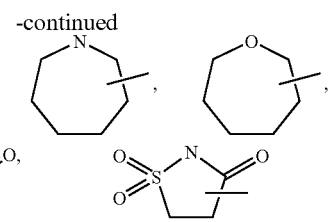

and the like. The above groups may include 1 to 4 substituents such as alkyl, halo, oxo and/or any of the aryl substituents set out herein. In addition, any of the above rings can be fused to a cycloalkyl, aryl, heteroaryl or cycloheteroalkyl ring.

The term "heteroaryl" or "heterocyclicaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, such as

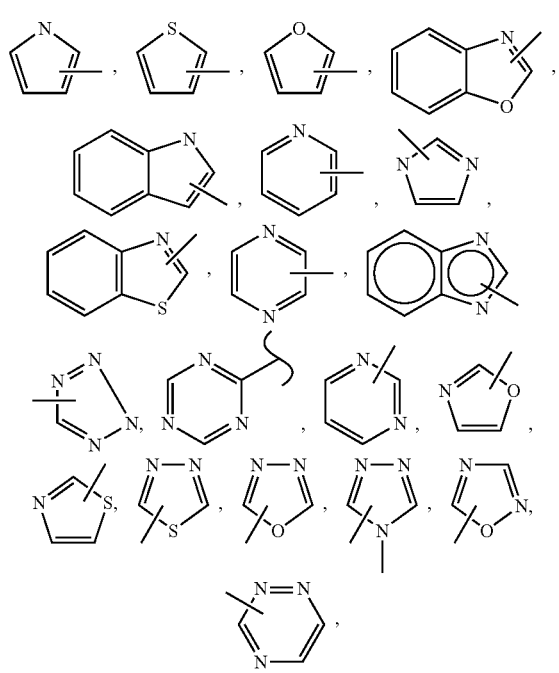

and the like.

The heteroaryl groups may optionally include 1 to 4 substituents such as any of the aryl substituents set out herein. In addition, any of the above rings can be fused to a cycloalkyl, aryl, heteroaryl or cycloheteroalkyl ring.

The term "prodrug esters" of the formula I compounds includes esters of hydroxyls and phenols, such as acetate, benzoate, pivolate, stearoylate, isobutyrate, and the like as known in the art.

Methods of Preparation

The compounds of the present invention may be prepared according to the following general synthetic reaction schemes as well as relevant published literature procedures that may be used by one skilled in the art. Exemplary reagents, procedures and conditions for these reactions appear hereinafter and in the working examples. Starting materials are commercially available or can be readily prepared by one of ordinary skill in the art using known methods. Unless otherwise specified the various substituents of the compounds are defined in the same manner as the formula I.

SCHEME I

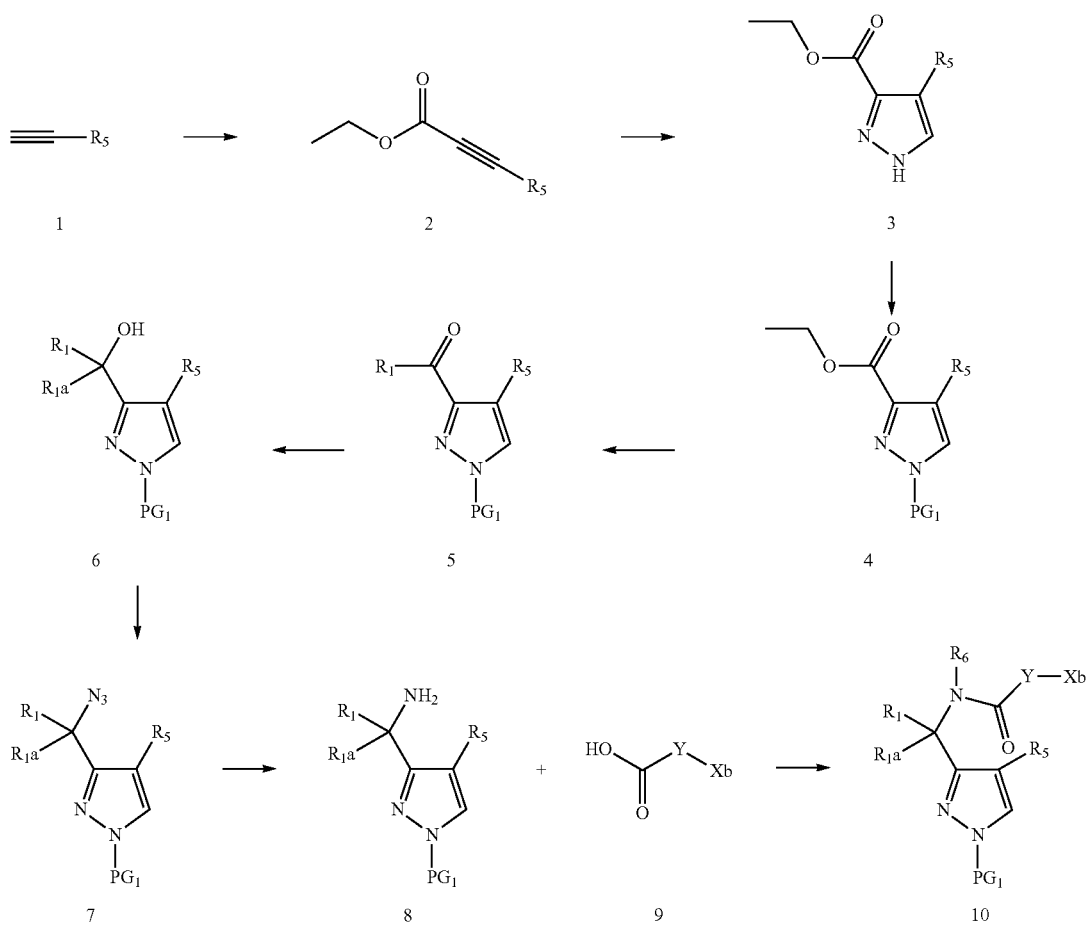

Preparation of compounds exemplified by formula can be prepared from t-butylsilyloxy-3-butyne by lithiation followed by treatment with alkyl chloroformates to provide alkynyl ester 2. Cycloaddition of 2 with diazomethane provided pyrazole 3, which was protected with a protecting group PG1 to give pyrazole ester 4. Treatment of 4 with a grignard reagent provided ketone 5, which was reduced to alcohol 6. Reaction of 6 with phenylphosphorylazide led to azide 7, which upon hydrogenation gave amine 8. 10 can be prepared via the aminolysis of a compound of formula 9 using an appropriate carboxylic acid activating reagent and amine 8 in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide.

SCHEME Ia

Scheme Ia describes the preparation of analogs wherein $R_5$ is defined as $(CH_2)n$—OPG (n = 1-5)

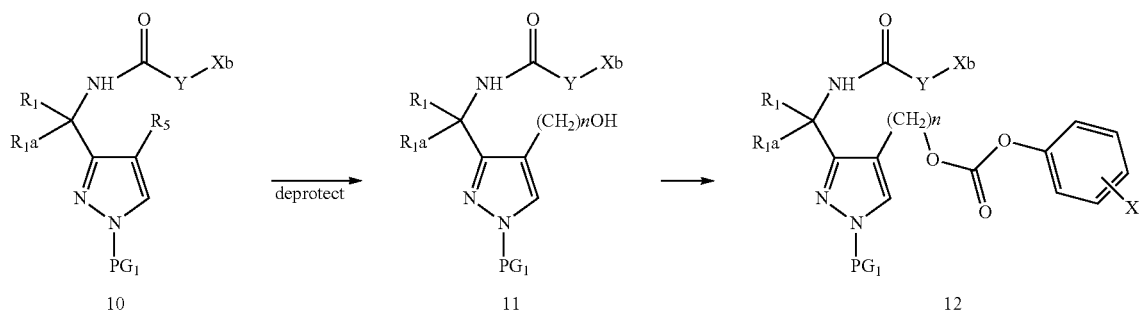

Where $R_5 =$ —$(CH_2)n$OPG
n = 1-5, PG1 = a protecting group

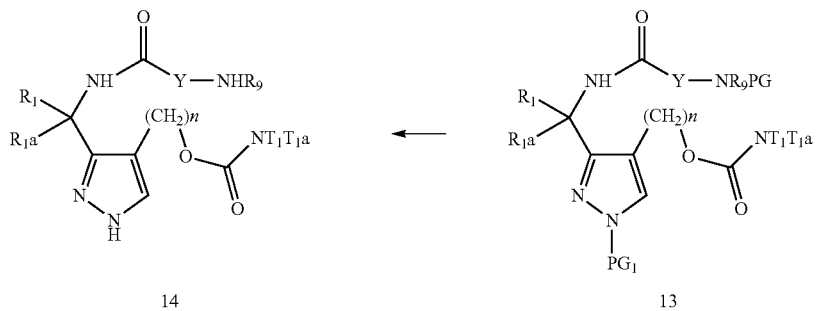

Selective deprotection of PG in 10 gave 11, which upon treatment with pyridine and substituted phenyl chloroformate (X is hydrogen or an electron withdrawing group) gave the carbonate 12. Treatment with primary or secondary amines led to compound 13. Deprotection in strong, non-aqueous acids (such as trifluoroacetic acid in dichloromethane or hydrogen chloride in dioxane) provided compounds of the formula 14.

SCHEME II

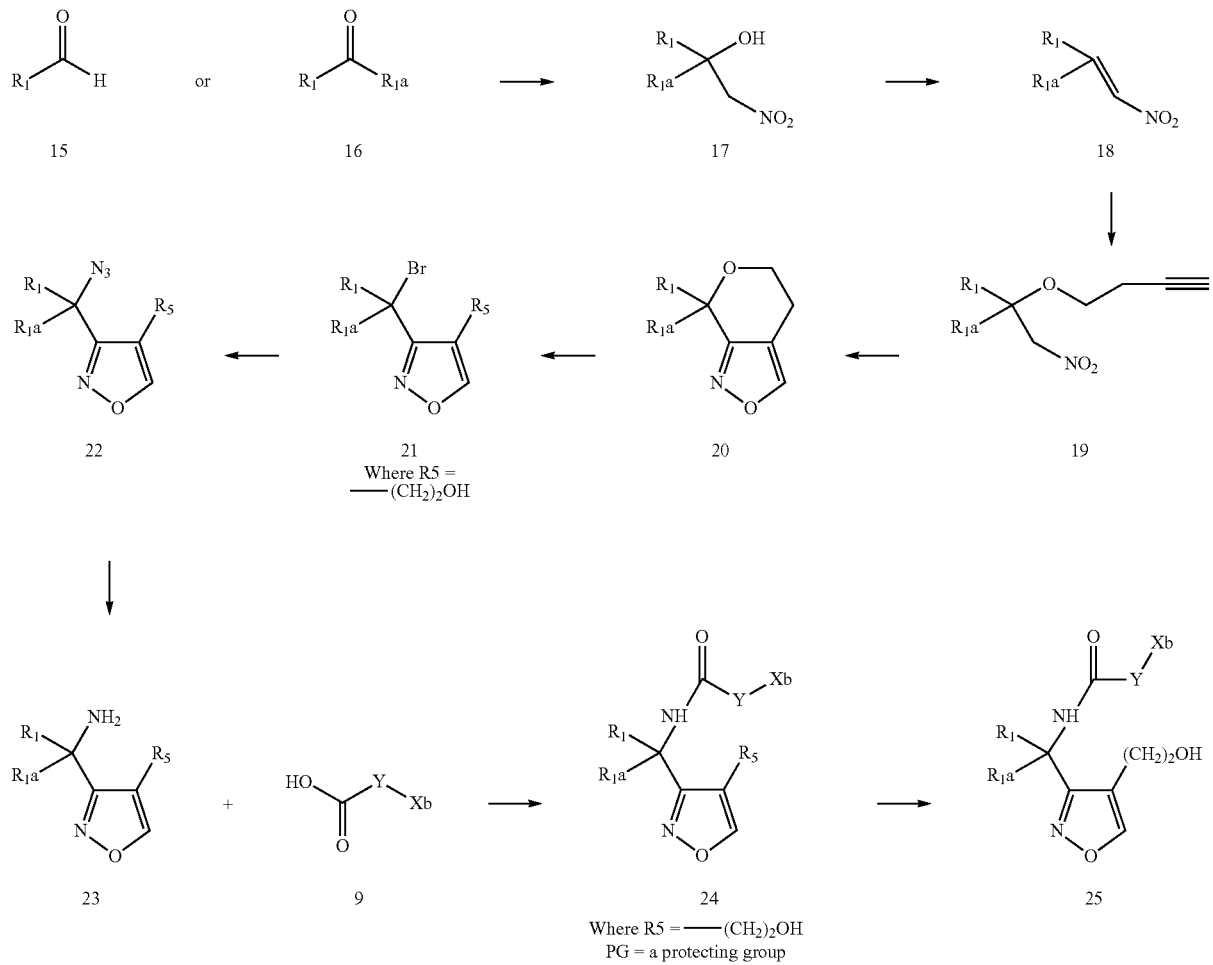

-continued

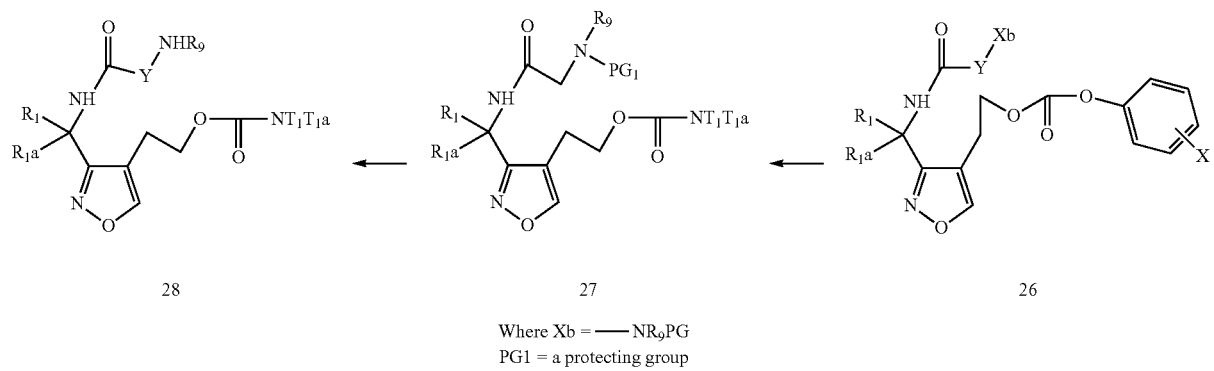

Where Xb = —NR$_9$PG
PG1 = a protecting group

Compounds of type 28 are prepared as described in scheme II. 4-Phenyl butanal or other aldehydes 15 or ketones 16 upon treatment with nitromethane and catalytic amounts of potassium t-butoxide give β-hydroxy nitroalkane 17. Treatment of 17 by standard methods provided nitroalkene 18. Treatment of 18 with sodium anion of 3-butyn-1-ol led to the ether 19 which, when treated with excess phenylisocyanate and catalytic triethylamine at ambient temperature, provided cyclohexaoxaisoxazole 20. Treatment of 20 with borontribromide gave bromoalcohol 21. Reaction of 21 with excess sodium azide in aqueous acetone provided azide 22, which was reduced to amine 23 by treatment with triphenylphosphine in aqueous tetrahydrofuran. 24 can be prepared via the aminolysis of a compound of formula 9 using an appropriate carboxylic acid activating reagent and amine 23 in an inert solvent. Treatment of 25 with pyridine and substituted phenyl chloroformate (X is hydrogen or an electron withdrawing group) gave the carbonate 26. Treatment with primary or secondary amines led to compound 27. Deprotection in strong, non-aqueous acids (such as trifluoroacetic acid in dichloromethane or hydrogen chloride in dioxane) provided compounds of the formula 28.

SCHEME III

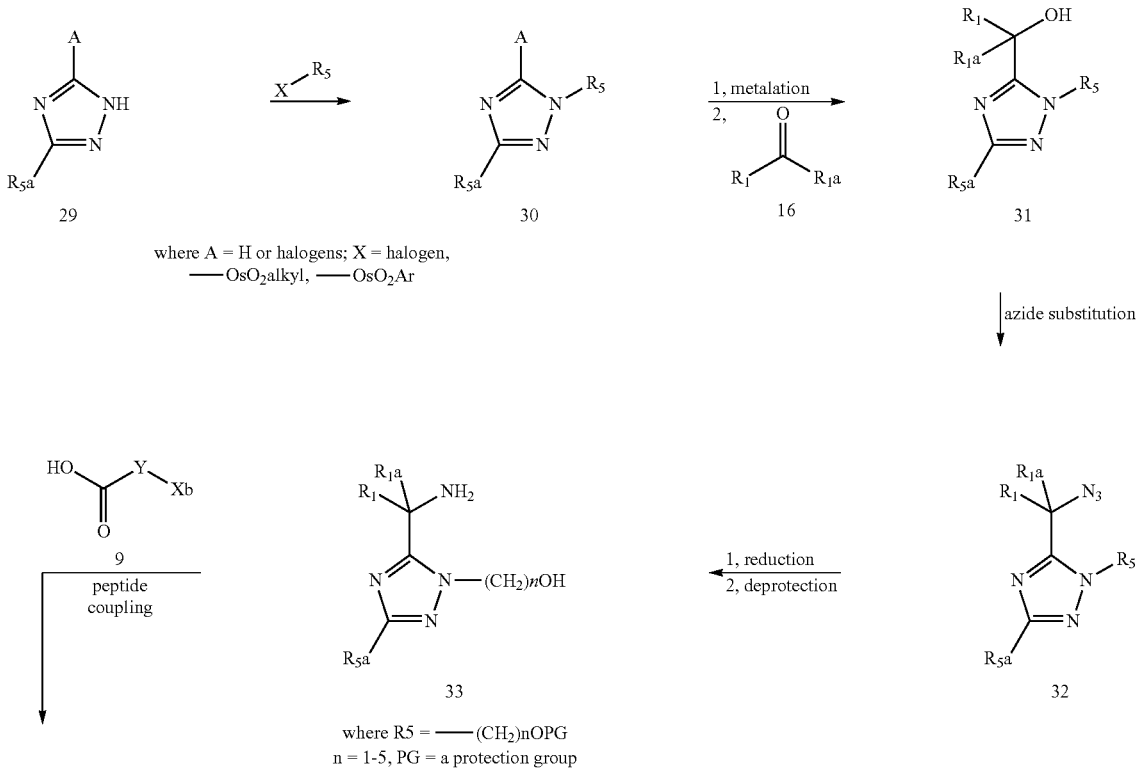

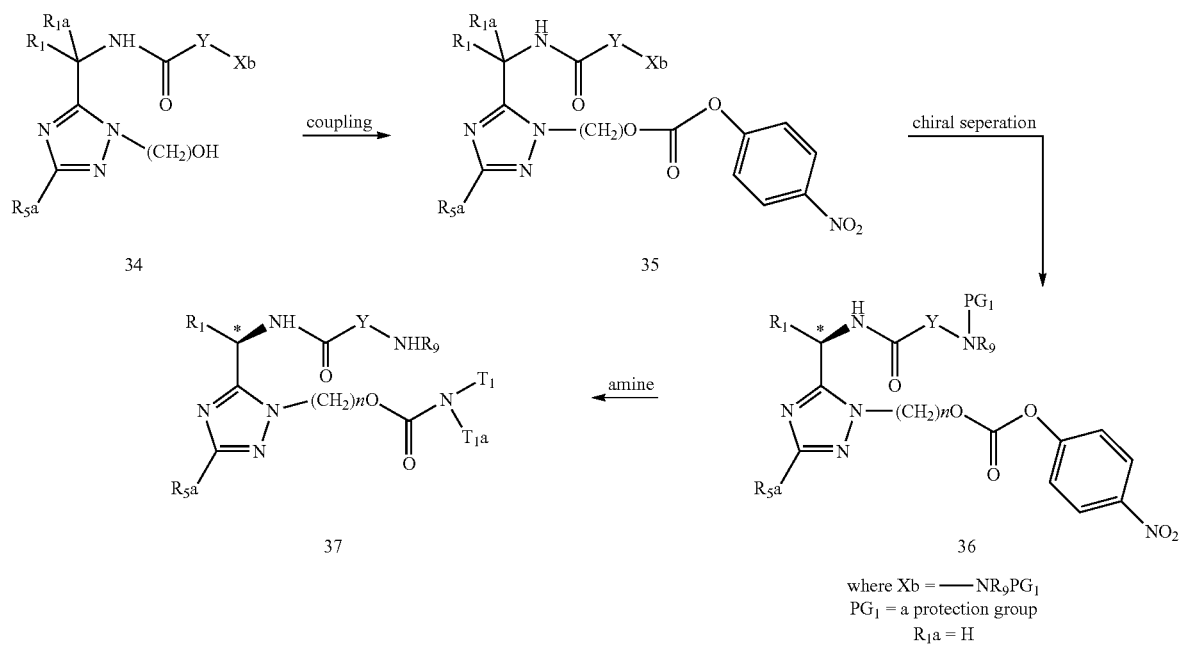

Preparation of compounds exemplified by formula 37 can be prepared by alkylation of 29 (X=Br) followed by metallation and treatment with aldehyde or ketone 16 to give 31. 31 were subjected to azide substitution to provide the azide 32, which was reduced to the amine and the protecting group was deprotected. 34 can be prepared via the coupling of compound 9 with 33 using an appropriate carboxylic acid activating reagent in an inert solvent. 34 upon treatment with pyridine and substituted phenyl chloroformate gave the carbonate 35. 35 were subjected to chiral separation using preparative HPLC to give 36. Treatment with primary or secondary amines led to compound 37.

SCHEME IIIa

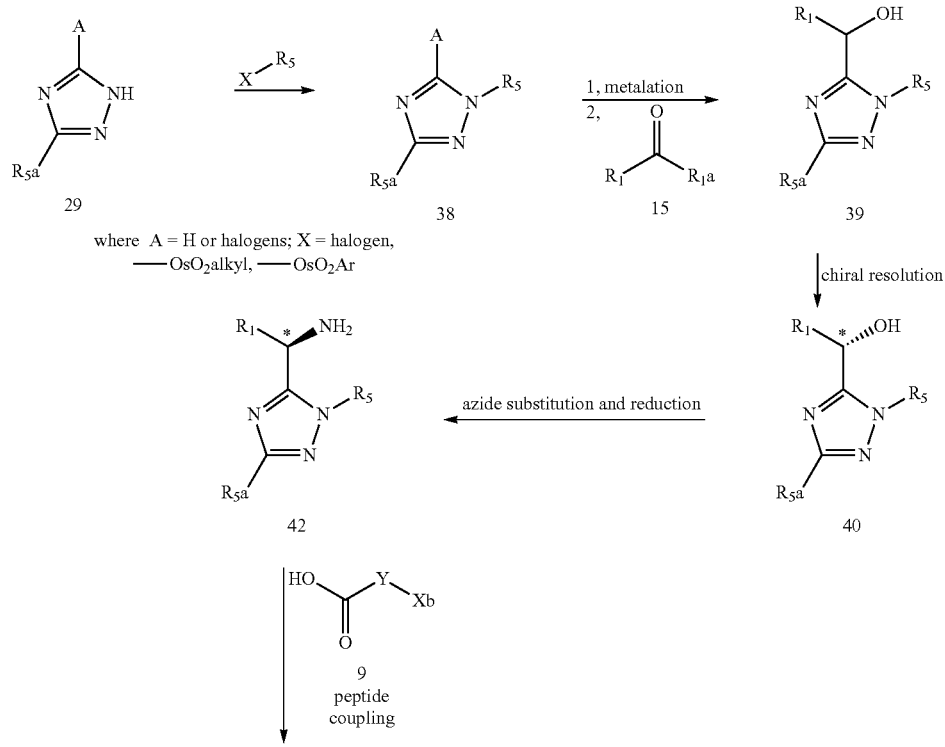

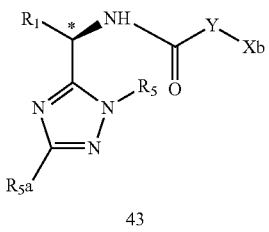

43

Preparation of compounds exemplified by formula 43 can be prepared by alkylation of 29 (X=Br) followed by metallation and treatment with aldehyde 15 to give alcohol 39. chiral alcohol 40 can be prepared by the chiral resolution of alcohol 39 or its ester derivatives. Chiral resolutions are done by one of ordinary skill in the art for example by method of crystallization or enzyme resolution.

SCHEME IIIb

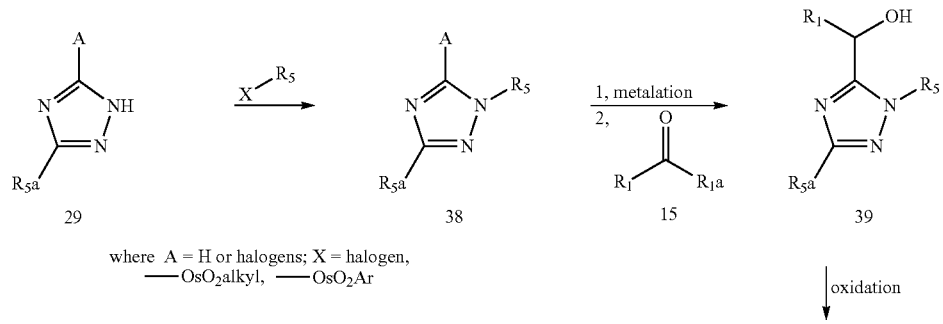

where A = H or halogens; X = halogen, —OsO$_2$alkyl, —OsO$_2$Ar

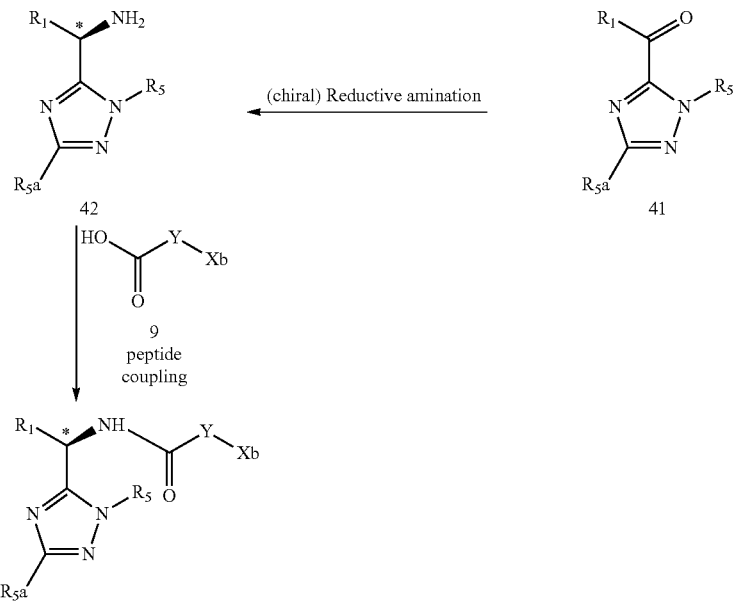

Alternatively, compounds exemplified by formula 43 can be also prepared by alkylation of 29 (X=Br) followed by metallation and treatment with aldehyde 16 to give 39. Compound 41 was prepared by oxidation of compound 39 using ordinary skill in the art. Compound 41 was subjected to chiral reductive amination using asymmetric catalytic process to provide 41.
SCHEME IV
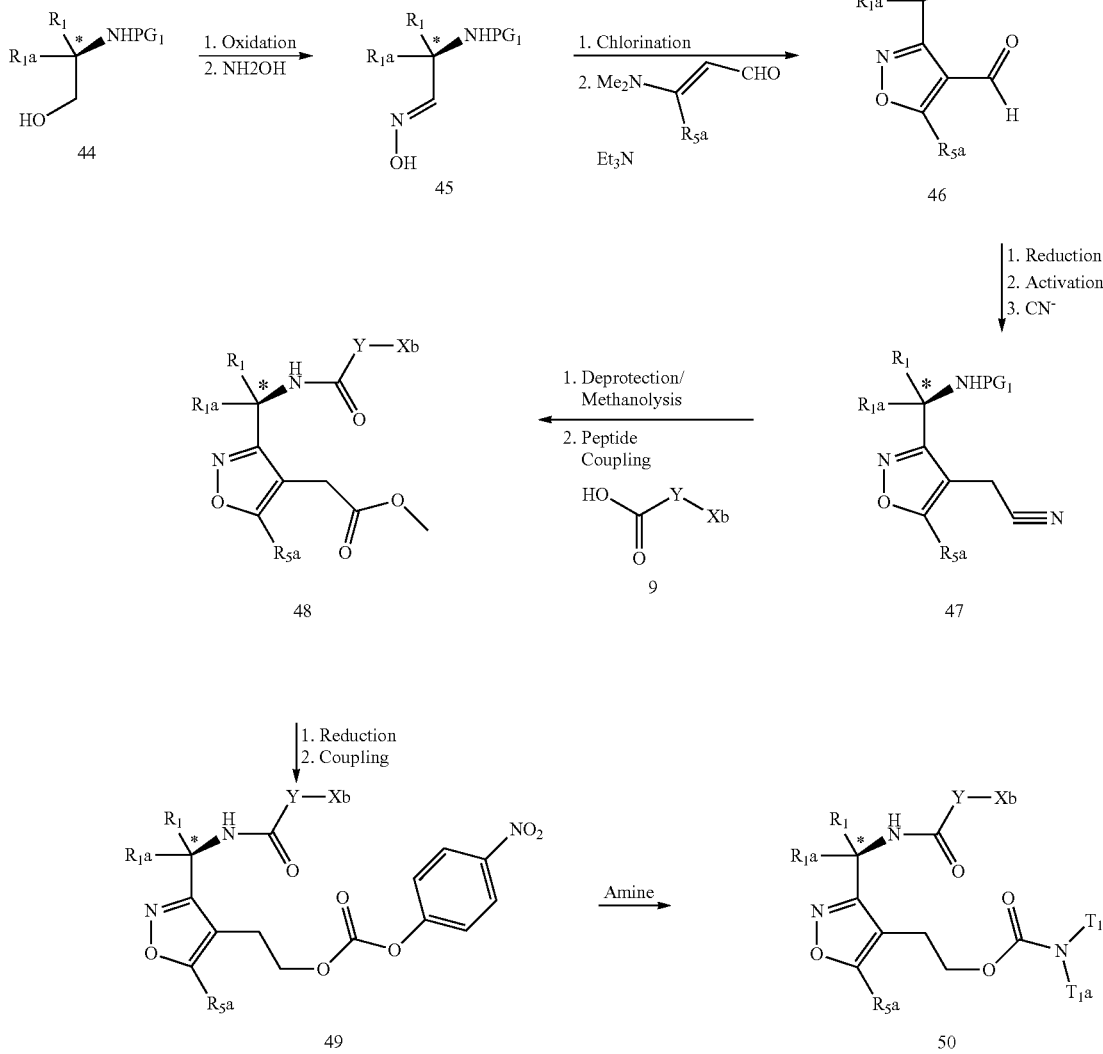
SCHEME IVa
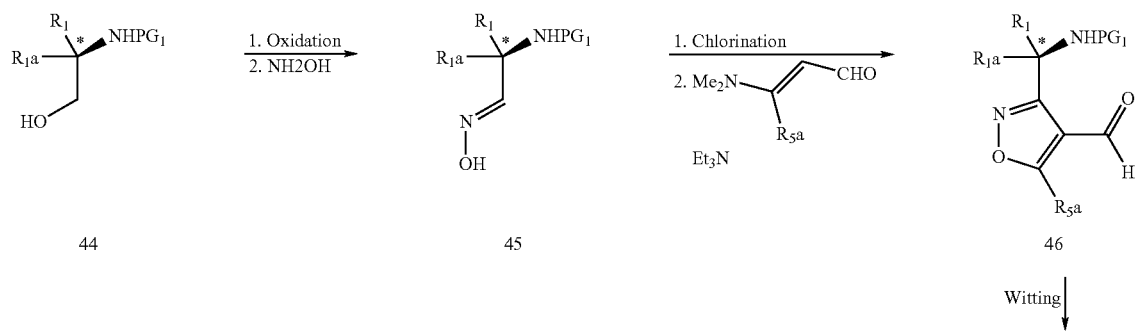

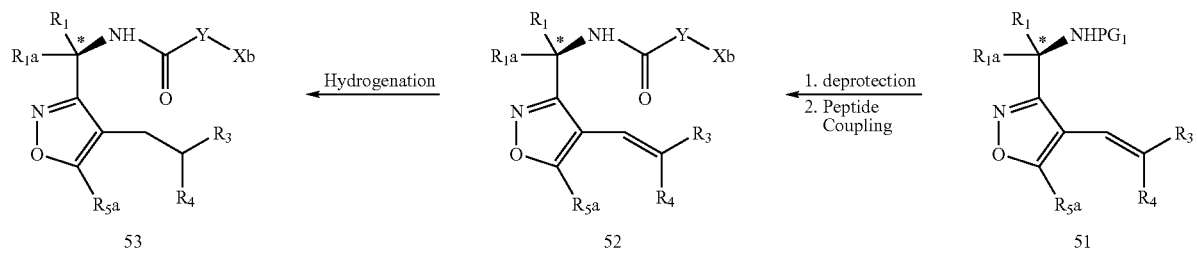

Compounds exemplified by formula 50 (scheme IV) and 53 (SchemeIVa) can be prepared as follows:

Oxidation of the alcohol 44 to aldehyde followed by treatment with hydroxylamine hydrochloride in pyridine afforded oxime 45. Oxidation to aldehyde of alcohol 44 can be carried out under conditions described in Konradi, A. W. et al., *J. Am. Chem.*, 116, 1316-1323 (1994).

Isoxazoles of formula 46 were prepared according to a modification of the procedure disclosed in Jones, R. C. F. et al., *Synlett* S1, 873-876 (1999). Modifications to this procedure are included hereinafter in the working examples.

Nitrile 47 was obtained from aldehyde 46 by the sequence reduction, activation of the resulting alcohol and displacement by cyanide, which is known in the art. Optimally the reduction to alcohol is carried out with sodium borohydride and the activation, as a mesylate, by treatment with methanesulfonyl chloride and triethylamine.

Deprotection in these schemes may be carried out by procedures generally know in the art. See, for example, T. W. Greene, Protecting groups in Organic Synthesis, Third Edition, 1999. PG in these schemes denotes a nitrogen protecting group, optimally BOC. The BOC group can be removed under acidic conditions, optimally HCl or trifluoroacetic acid. If HCl in methanol is used to remove the BOC group in 47, simultaneous methanolysis of the cyano group occurs.

In these schemes, amide bond forming (peptide coupling) reaction is conducted under standard peptide coupling procedures known in the art. Optimally the reaction is conducted in solvents such as dimethylformamide (DMF) and 1,2-dichloroethane (1,2-DCE) at 0° C. to room temperature using 1-ethyl-3-(3-dimethylaminopropyl) carbodiimide (EDAC) or (WSC), 1-hydroxybenzotriazole hydrate (HOBt) or 1-hydroxy-7-azabenzotriazole (HOAT) and a base such as triethyl amine.

Reduction of the ester 48 followed by coupling provided the carbonate 49. Reduction of ester 48 to its corresponding alcohol can be accomplished by using lithium or calcium borohydride. Treatment of the alcohol with pyridine and substituted phenyl chloroformate (X is hydrogen or a withdrawing group) gave the carbonate 49. Treatment with primary or secondary amines led to compound 50.

The coupling of the aldehyde 46 with a phosphorane to yield the olefin 51, covered in Scheme IVa, can be performed under the known Witting reaction conditions in the literature such as described in Quintela, J. M. et al., *Tetrahedron*, 54 8107-8122 (1998).

Hydrogenation of the olefin 52 to alkane 53, in scheme IVa, can be carried out with $H_2$ in the presence of palladium as a catalyst. The working examples, enclosed hereinafter, should be consulted to achieve selective reduction of the double bond versus the cyano group and the isoxazole ring.

SCHEME Va

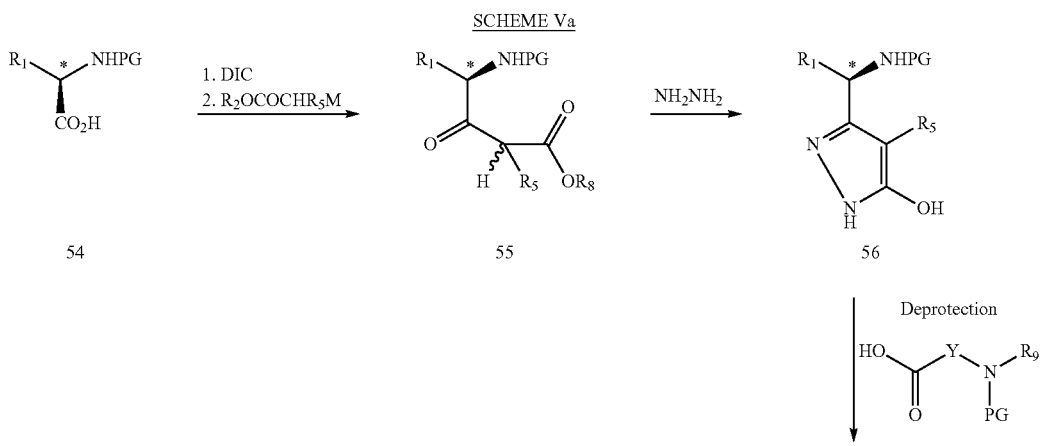

-continued

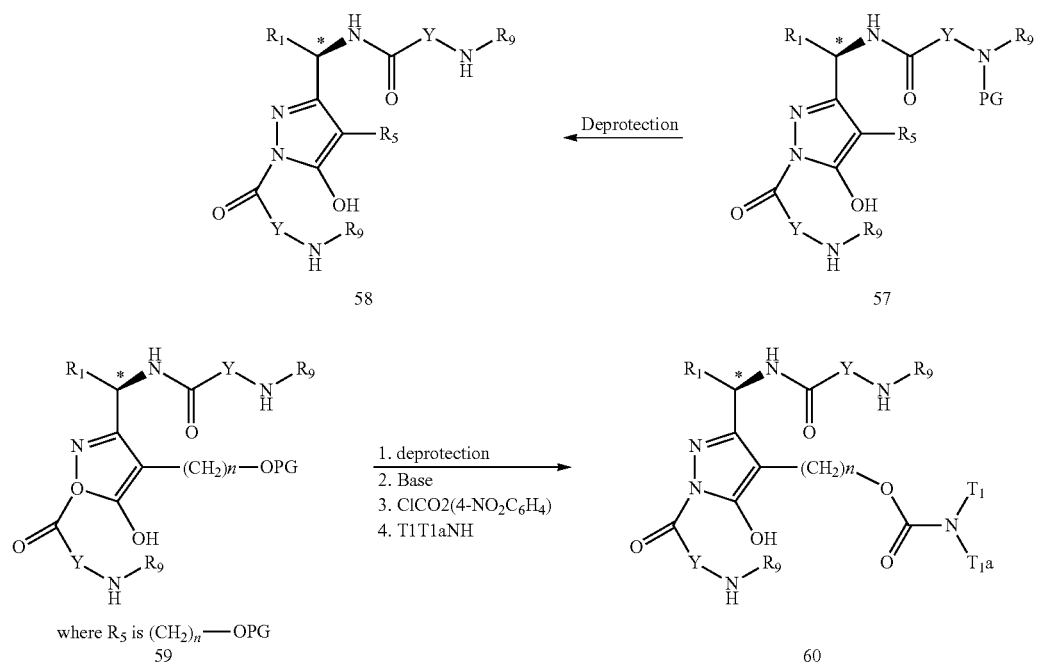

Treatment of protected amino acid 54 with diimidazole-carbonyl followed by addition of the α-lithium anion of an ester or lactone provides ketoester 55. Reflux of 55 with excess hydrazine hydrate in aqueous ethanol leads to pyrazole 56. Removal of the Boc group using standard conditions followed by coupling of a suitably protected amino acid in excess led to 57 and deprotection under standard conditions led to 58. In addition, 59, where $R_5=(CH_2)_2OPG$ can be deprotected by standard methods and treated with a mixture of base and 4-nitrophenyl chloroformate to give an activated carbamate. Further treatment with T1T1aNH leads to carbamate 60.

SCHEME Vb

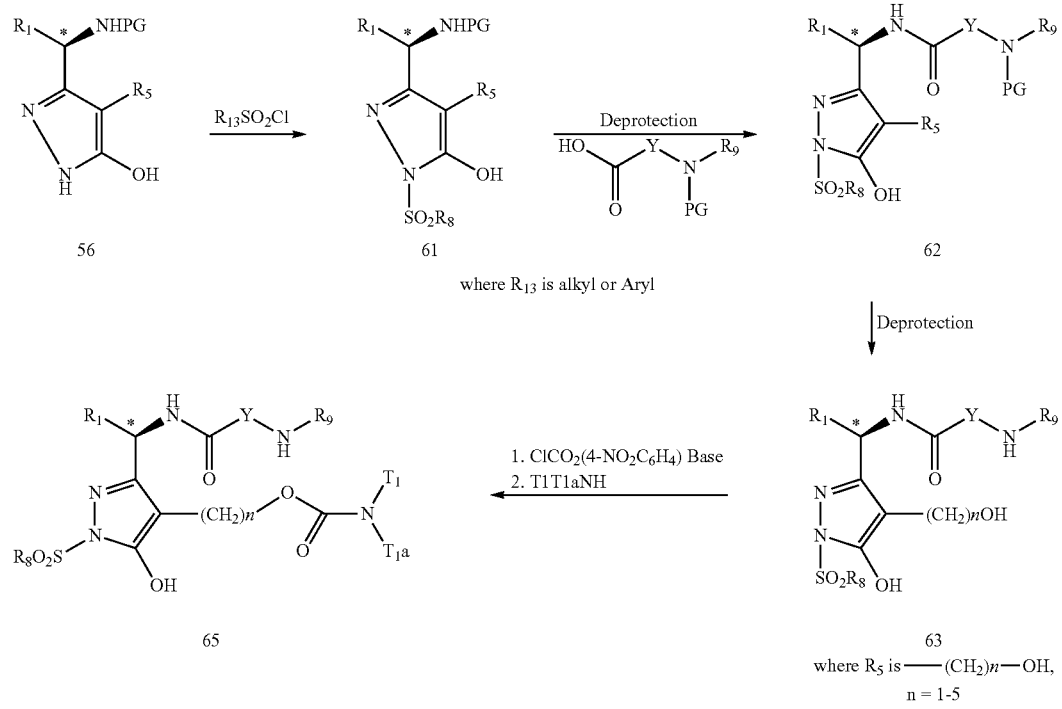

Furthermore, treatment of 56 with sulfonylchloride $R_8SO_2Cl$ provides sufonylated pyrazole 61, which, upon deprotection and coupling of a suitably protected amino acid under standard conditions, provides 62. Deprotection and treatment with 4-nitrophenyl chloroformate as described above in Scheme Vb leads to 65.

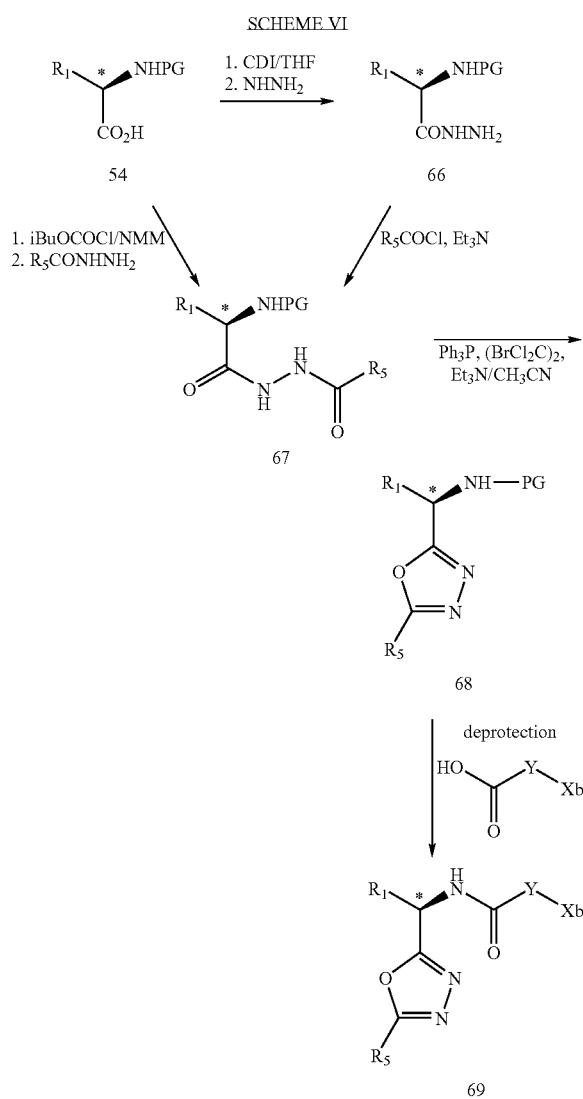

SCHEME VI

Diacylated hydrazide 67, obtainable either by forming the mixed anhydride of protected amino acid 54 and reacting this with the hydrazide $R_5CONHNH_2$ or by preparing the unsubstituted hydrazide 66 and subsequent reaction with acylchloride, was cyclized with triphenylphosphine and dibromotetrachloroethane under basic conditions in acetonitrile to provide oxadiazole 68. Deprotection and coupling using standard methods leads to 69.

Other heterocycles can be prepared by methods known to those skilled in the art and by methods found in A. Katritzky, Comprehensive Heterocyclic Chemistry, Volume 1 and Volume 2, Elseveir.

General Experimental

HPLC conditions for examples 4, 5, 6, 7, 8, 9, 10, 11, 12, 13 and 14: The term HPLC refers to a Shimatzu high performance liquid chromatography using a 4 minute gradient of 0-100% solvent B [MeOH:H2O:0.2% H3PO4] with a 1 min. hold, an ultra violet (uv) detector set at 220 nM, and using a column (4.6×50 mm) packed with YMC C18 5 micron resin. A mixture of solvent A (10% MeOH/90% H2O/0.2% TFA) and solvent B (90% MeOH/10% H2O/0.2% TFA) are used for preparative reverse phase HPLC in an automated Shimatzu system. The preparative columns are packed with YMC ODS C18 5 micron resin. The preparative column for the chiral preparative HPLC was packed with Chiralpak AD 2 µM (5×50 cm) using Isopropyl alcohol and hexane as the solvents.

HPLC conditions for Examples 1, 2, 3, 15, 16, 17, 18, 19, 20 and 21: The term HPLC refers to a Shimatzu high performance liquid chromatography using a 8 minute gradient of 0-100% solvent B [CH3CN:H2O:0.1% TFA] with a 1 min. hold, an ultra violet (uv) detector set at 220 nM, and using a column (4.6×50 mm) packed with Zorbax SB C18. A mixture of solvent A (10% CH3CN/90% H2O/0.2% TFA) and solvent B (90% CH3CN/10% H2O/0.1% TFA) are used for preparative reverse phase HPLC in an automated Shimatzu system. The preparative columns are packed with YMC ODS C18 5 micron resin.

Utilities and Combinations

Utilities

The growth hormone releasing compounds of formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed compounds of formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of formula I of the invention is in combination with parathyroid hormone or bisphosphonates, such as MK-217 (alendronate), in the treatment of osteoporosis.

A still further use of the disclosed compounds of formula I is in combination with estrogen, testosterone, a selective estrogen receptor modulator, such as tamoxifen or raloxifene, or a selective androgen receptor modulator, such as disclosed in Edwards, J. P. et al., *Bio. Med. Chem. Let.*, 9, 1003-1008 (1999) and Hamann, L. G. et al., *J. Med. Chem.*, 42, 210-212 (1999), for the treatment of aspects of Metabolic Syndrome, maintenance of muscle strength and function in elderly humans, reversal or prevention of frailty in elderly humans, stimulation and increase in muscle mass and muscle strength, attenuation of protein catabolic response after a major operation or trauma; reducing cachexia and protein loss due to chronic illness such as cancer or AIDS; improvement in muscle mobility, and maintenance of skin thickness.

A further use of the compounds of this invention is in combination with progestin receptor agonists ("PRA").

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself.

To those skilled in the art, it is well known that the current and potential uses of growth hormone are varied and multitudinous. Thus, compounds of formula I can be administered for purposes stimulating release of endogenous growth hormone and would thus have similar effects or uses as growth hormone itself. Compounds of formula I are useful for stimulation of growth hormone release (e.g., in the elderly); maintenance of muscle strength and function (e.g., in the elderly); reversal or prevention of fraility or age-related functional decline ("ARFD") in the elderly; prevention of catabolic side effects of glucocorticoids; prevention and treatment of osteoporosis; treatment of chronic fatigue syndrome (CFS); treatment of acute fatigue syndrome and muscle loss following election surgery; stimulation of the immune system, including improvement of immune response to vaccination; acceleration of wound healing; accelerating bone fracture repair (such as accelerating the recovery of hip fracture patients); accelerating healing of complicated fractures, e.g. disctraction osteogenesis; acceleration of tooth repair or growth; maintenance of sensory function (e.g., hearing, sight, olefaction and taste); treatment of wasting secondary to fractures; treatment of growth retardation; treatment of growth retardation resulting from renal failure or insufficiency; treatment of cardiomyopathy; treatment of wasting in connection with chronic liver disease; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of wasting in connection with chronic obstructive pulmonary disease (COPD); treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of growth retardation associated with the Prader-Willi syndrome and Turner's syndrome; increasing the growth rate of a patient having partial growth hormone insensitive syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients; treatment of osteochondrodysplasias; treatment of Noonan's syndrome; treatment of schizophrenia; treatment of depression; improvement of cognitive function (e.g., treatment of dementia; treatment of Alzheimer's disease; treatment of delayed wound healing and psychosocial deprivation; treatment of catabolism in connection with pulmonary dysfunction and ventilator dependency; treatment of cardiac dysfunction (e.g. associated with valvular disease, myocarial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; adjuvant treatment for ovulation induction; stimulation of thymic development and prevention of the age-related decline of thymic function; treatment of immunosuppressed patients; treatment of sarcopenia; treatment of wasting in connection with AIDS; treatment of wasting in connection with multiple sclerosis or other neurodegenerative disorders; improvement in muscle strength, mobility, maintenance of skin thickness; hair/nail growth; treatment of metabolic homeostasis and renal homeostasis (e.g., in the frail elderly); stimulation of osteoblasts, bone remodelling and cartilage growth; regulation of food intake; stimulation of the immune system in companion animals and treatment of disorders of aging in companion animals; promoting growth in livestock; stimulation of wool growth in sheep; increasing milk production in livestock; treatment of insulin resistance including NIDDM, in mammals (e.g. humans); treatment of insulin resistance in the heart; improvement of sleep quality and correction of the relative hyposomatotropism of senescence due to high increase in REM sleep and a decrease in REM latency; treatment of hypothermia; treatment of frailty such as that associated with aging; treatment of congestive heart failure; treatment of hip fractures; treatment of immune deficiency in individuals with a depressed T4/T8 cell ratio; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in elderly); enhancing the activity of protein kinase B (PKB); improvement of the overall pulmonary function; treatment of sleep disorders; and the treatment of the catabolic state of prolonged critical illness. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

Combinations

The compounds of the present invention may be employed alone or in combination with each other and/or other growth hormone secretagogues or other suitable therapeutic agents useful in the treatment of the aforementioned disorders including: anti-diabetic agents; anti-osteoporosous agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroesopheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519, 079 filed Mar. 6, 2000, PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Compounds of the present invention may further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

EXAMPLES

Example 1

1-{1-[3-(2-Cyclopropylmethylcarbamoyloxy-ethyl)-1H-pyrazol-4-yl]4-phenyl-butylcarbamoyl}-1-methyl-ethyl-ammonium

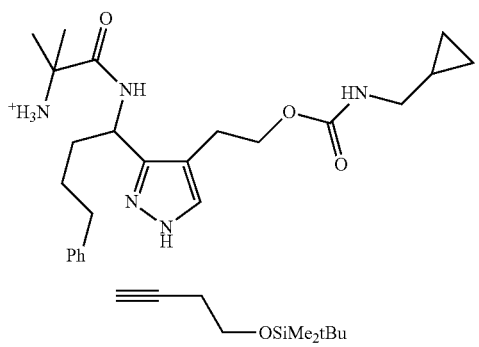

1A

To a 60% dispersion of NaH in mineral oil(1.2 g, 30 mmol,) in THF (25 m) at r.t. was added but-3-yn-ol (2.03 g, 29.0 mmol) dropwise via syringe over 10 min. The mixture was stirred for 30 min followed by addition of t-butyldimethylsilyl chloride (4.3 g, 29.0 mmol) in 5 ml of THF. After 1 h the mixture was quenched with aqueous saturated ammonium chloride solution and extracted with pentane. The extracts were dried, filtered and concentrated. The residue was distilled (58-60° C., 10 torr) to give 1A (3.6 g, 68%).

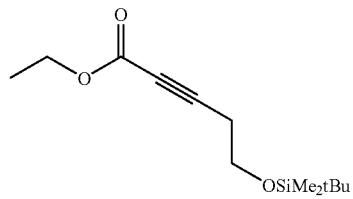

1B

To a stirred solution of 1A (3.3 g, 18 mmol) in 20 ml THF at −60° C. was added of n-butyllithium (7.2 ml, 18 mmol, 2.5M in hexane) dropwise over 10 min. After stirring the mixture for 30 min, ethyl chloroformate (1.95 ml, 20 mmol) was added at a rate to keep the temperature below −55° C. The mixture was allowed to warm to 0° C. over 2 h, quenched with saturated ammonium chloride solution and extracted with EtOAc. The extracts were dried, filtered and concentrated. Purification by flash chromatography on silica gel (47:53 CH$_2$Cl$_2$/hexanes as elutant) gave 1B as a colorless oil (3.93 g, 85%).

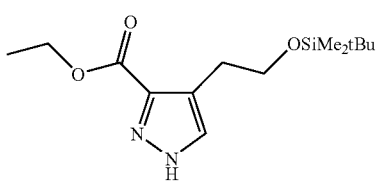

1C

To a stirred solution of diazomethane (prepared from Diazald (2 g, 10 mmol)) in ether (25 ml) at 0° C. was added 1B (2 g, 7.8 mmol). After stirring for 75 h in a bath maintained at −2 to +2° C., a few drops of acetic acid were added to disperse excess diazomethane. The mixture was washed with saturated NaHCO3, dried, filtered and concentrated. Purification by flash chromatography on silica gel (1:4 EtOAc/Hexane as elutant) gave a mixture of 4- and 5-positional isomers of 1C (890 mg, 66%).

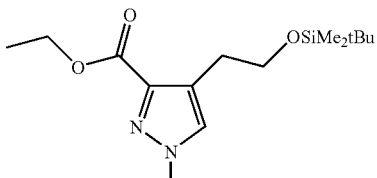

1D

To a stirred solution of 1C (940 mg, 3.15 mmol) in 10 ml THF was added NaH (128 mg, 3.2 mmol, 60% dispersion in mineral oil) in portions. After stirring the mixture for 15 min 2-(trimethylsilyl)methoxymethyl chloride(0.054 ml, 0.3 mmol) was added. Additional stirring for 1 h was followed by quenching with aqueous saturated ammonium chloride solution and extraction with CH$_2$Cl$_2$. The extracts were dried, filtered and concentrated. Purification by flash chromatography on silica gel (2:98 ether/CH$_2$Cl$_2$ as elutant) provided 1D (890 mg, 66%).

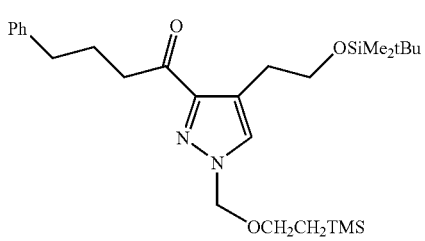

1E

A stirred solution of 3-phenylpropylmagnesium bromide (prepared from 3-phenylpropyl bromide and Mg in ether, 4.7 ml, ~4 mmol) was evaporated in situ and redissolved in toluene (10 ml) TEA (1.7 ml, 12.2 mmol) was added and the mixture cooled to −30° C. After 15 min, a solution of 1D (825 mg, 1.92 mmol) was added and the reaction was stirred for 1 h at −10° C. The mixture was quenched with aqueous saturated ammonium chloride solution and extracted with EtOAc. The extracts were combined, dried, filtered and concentrated. Purification by flash chromatography on silica gel (ether/CH$_2$Cl$_2$ as elutant) gave 1E as a colorless oil (635 mg, 66%).

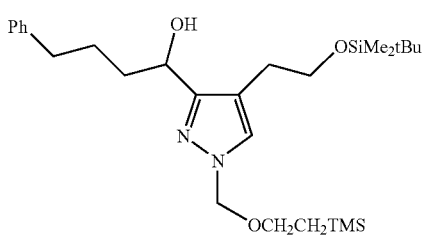

1F

To a stirred solution of 1E (458 mg, 0.9 mmol) in THF (3 ml) at r.t. was added Lithium aluminum hydride (1 ml, 1 mmol, 1M in THF). After stirring for 10 min, the reaction was quenched with aqueous saturated NaCl and extracted twice with EtOAc. The extracts were combined, dried and filtered through silica gel to provide 1F as a colorless oil (436 mg, 95%).

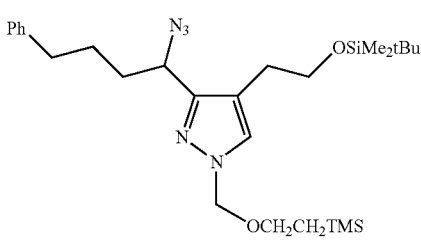

1G

To a solution of 1F (432 mg, 0.86 mmol) & triphenylphosphine (450 mg, 1.6 mmol) in THF (3 ml) at 0° C., was added diethyl diazacarboxylate (DEAD) (0.27 ml, 1.6 mmol) dropwise. After stirring for 10 min, diphenylphosphoryl azide was added. After 1 h the mixture was diluted with EtOAc, washed with aqueous saturated ammonium chloride, dried, filtered and concentrated. Purification by flash chromatography on silica gel (7:93 EtOAc/hexane as elutant) gave 1G as a colorless oil (165 mg, 36%).

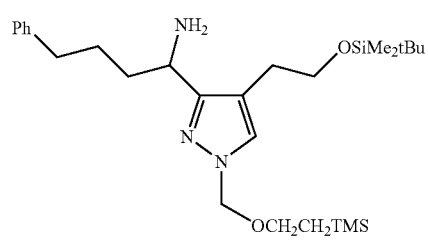

1H

A slurry of 10% Pd—C catalyst(16 mg of Pd by weight) & 1G (165 mg, 0.31 mmol) in 15 ml of EtOH was stirred under hydrogen atmosphere at atmospheric pressure for 24 h. The solution was then filtered and concentrated to give 1H as a colorless oil (154 mg, >99%).

1I

To Boc-2-aminoisobutyric acid (94 mg, 0.46 mmol) and 1-hydroxy-7-azabenzotriazole (63 mg, 0.46 mmol) in THF at 0° C. was added EDAC (88 mg, 0.46 mmol). After stirring for 30 min, a solution of 1H (154 mg, 0.3 mmol) in THF was added at 0° C. The mixture was stirred for 62 h, partially evaporated and extracted with ether. The extracts were dried, filtered and concentrated. Purification by flash chromatography on silica gel (1:6 EtOAc/CH$_2$Cl$_2$ as elutant) gave 1I as a colorless oil (121 mg, 55%).

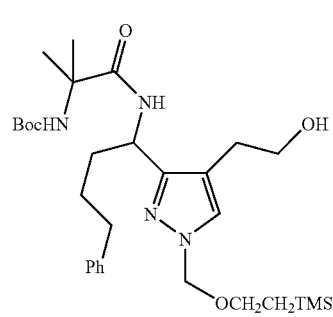

1J

To a stirred solution of 1I (120 mg, 0.17 mmol) in THF (2 ml) was added tetrabutylammonium fluoride (0.2 ml, 0.2 mmol, 1M in THF). After stirring for 1 h at r.t., the reaction was diluted with EtOAc, washed with ammonium chloride, dried, filtered and concentrated. Purification by flash chromatography on silica gel (3:2 EtOAc/CH$_2$Cl$_2$ as elutant) gave 1J as a colorless oil (85 mg, 85%).

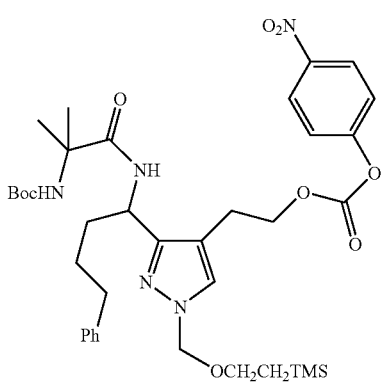

1K

To a solution of 1J (85 mg, 0.15 mmol) in THF (1 ml) at 0° C. was added pyridine (30 μl) and 4-nitrophenyl chloroformate (66 mg, 0.3 mmol) in CH₂Cl₂ (1 ml). After stirring at 0° C. for 1 h and then 3 h at r.t., the mixture was filtered & concentrated. Purification by flash chromatography on silica gel (1:6 EtOAc/CH₂Cl₂ as elutant) gave 1K as a colorless oil (94 mg, 857%).

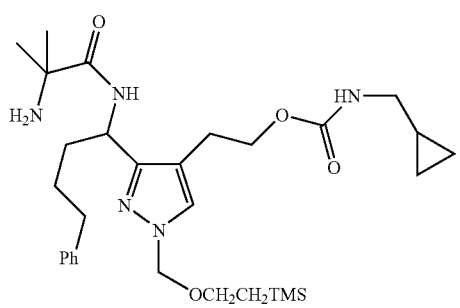

1L

To a solution of 1K (94 mg, 0.13 mmol) in THF (1 ml) was added cyclopropanemethylamine (15 ul, 0.17 mmol). After stirring the resulting yellow solution for 1 h, the mixture was diluted with EtOAc, washed with 1M NaOH, dried, filtered and concentrated. Purification by flash chromatography on silica gel (1:4 EtOAc/hexane as elutant) gave 1L as a colorless oil (65 mg, 77%).

Example 1

A solution of 1L (65 mg, 0.09 mmol) in CH₂Cl₂ (4.5 ml) and TFA (0.5 ml) was stirred for 4 h and then concentrated. The residue was redissolved in 1:1 CH₃CN/H2O & purified by preparative HPLC to give the title compound as a colorless oil (34.5 mg, 53%). MS (M+H) is 442; HPLC retention time 3.36 min Alternate Synthesis of Example 1

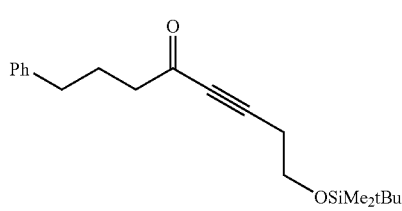

1M

A stirred solution of 1A (2.65 g, 14.4 mmol) was treated with N-methyl-N-methoxy-4-phenylbutanamide (2.83 g, 14.6 mmol) according to the method for 1B to provide 1M as a colorless oil (4.5 g, 96%).

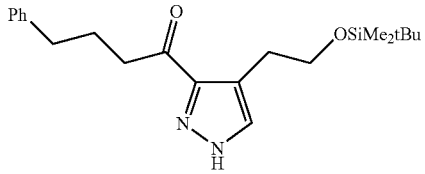

1N 1M (4.5 g, 13.8 mmol) was treated with a solution of diazomethane (prepared from Diazald (4 g, 18.4 mmol)) according to the method for 1C to provide 1N as a white solid (4.0 g, 78%).

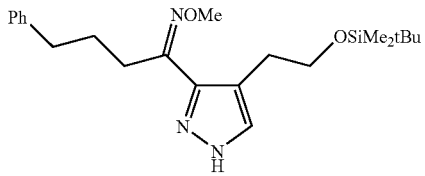

1O

To 1N (0.38 mg, 1.0 mmol) in ethanol (4 ml) was added methoxylamine hydrochloride (126 mg, 1.5 mmol) and sodium acetate (123 mg, 1.5 mmol). The mixture was refluxed for 4 hr, cooled, concentrated & extracted with 1:1 ether/hexane. Purification by flash chromatography on silica gel (1:7 EtOAc/CH₂Cl₂ as elutant) gave 1O as a colorless oil (350 mg, 87%).

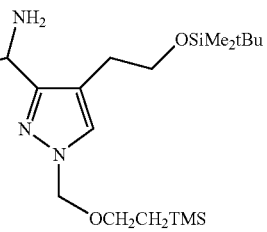

1P

To 1O (0.350 mg, 0.87 mmol) in THF (5 ml) was added boran-tetrahydrofuran complex (3.5 ml, 3.5 mmol, 1M in THF) and the mixture was refluxed for 8 h. The solution was then cooled and treated with methanol (10 ml). The resulting mixture was refluxed for 1 h and evaporated under reduced pressure. The residue was evaporated from methanol and from dichloromethane to give 1P as a colorless oil (315 mg, 97%).

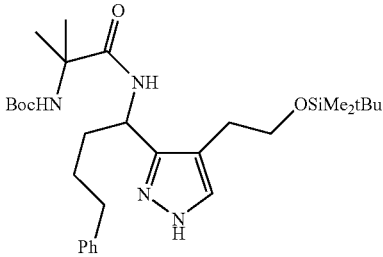

1Q 1Q was prepared using the method described in 1I substituting 1H with 1P (0.315 g, 0.84 mmol) and Boc-2-aminoisobutyric acid (0.256 g, 1.3 mmol). 1Q was obtained as a colorless oil (253 mg, 52%).

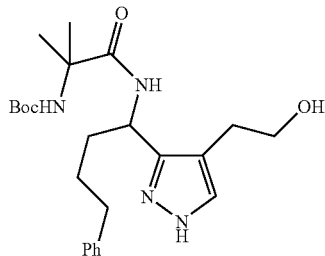

1R

To a stirred solution of 1Q (760 mg, 1.36 mmol) in MeOH (5 ml) was added 1M solution of HCl in MeOH (5 ml). After 30 min, the reaction was quenched by adding solid NaHCO₃ (320 mg). The mixture was concentrated partially and extracted with EtOAc, dried, filtered and concentrated. Purification by flash chromatography on silica gel (1:22 MeOH/EtOAc as elutant) gave 1R as a white solid (0.550 g, 92%).

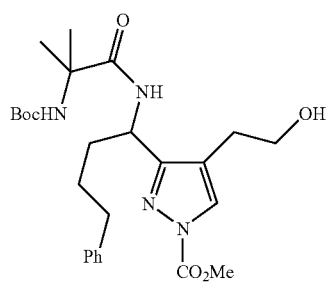

1S

To a stirred solution of 1R (400 mg, 0.9 mmol) in THF (3 ml) at 0° C. was added pyridine (74 µl, 0.92 mmol) and methyl chloroformate (71 µl, 0.92 mmol). After stirring for 1 h the mixture was quenched with ammonium chloride, extracted with EtOAc, dried, filtered and concentrated. Purification by flash chromatography on silica gel (1:3 CH2Cl2/EtOAc as elutant) gave 1S as a colorless oil (290 mg, 65%).

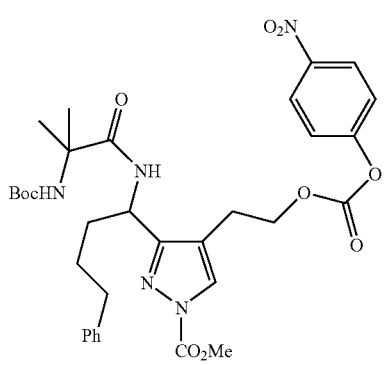

1T 1T was prepared using the method described in 1K substituting 1J with 1S (290 mg, 0.6 mmol) and 4-nitrophenyl chloroformate (120 mg, 0.6 mmol). 1T was obtained as a colorless oil (260 mg, 68%).

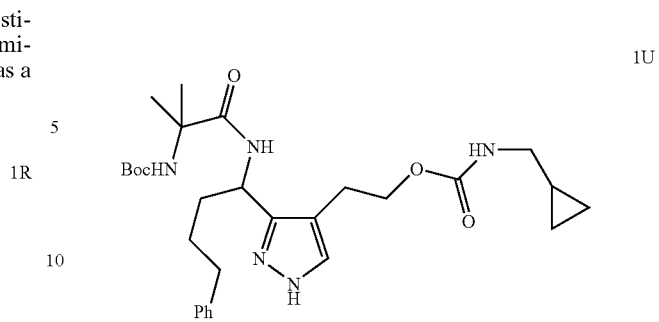

1U 1U was prepared using the method described in 1L substituting 1K with 1T (115 mg, 0.17 mmol) and cyclopropanemethyl amine (50 µl, 0.6 mmol). 1U was obtained as a colorless oil (72 mg, 77%).

Example 1

A solution of 1U (72 mg, 0.14 mmol) in 1 ml CH₂Cl₂ and 1 ml of a 4M HCl/dioxane solution was stirred for 2 h and then concentrated. The residue was dissolved in water and lyophilized to give a white foam (68 mg, 98%).

Example 2

Cyclopropylmethyl-carbamic acid 2-{3-[1-(2-amino-2-methyl-propionylamino)-4-phenyl-butyl]-isoxazol-4-yl}-ethyl ester

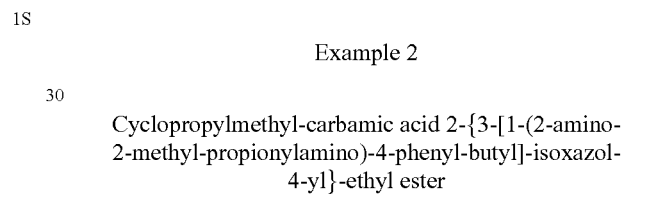

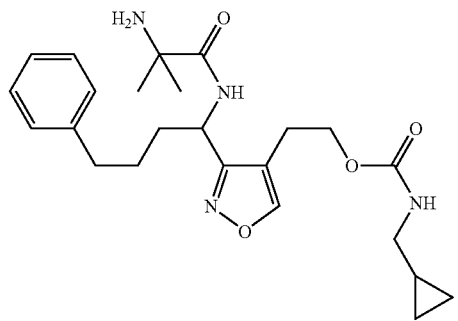

2A

To a stirred solution of oxalyl chloride (10.2 ml, 2M in CH₂Cl₂) in CH₂Cl₂ (35 ml) at −78° C. was added DMSO (2.8 ml in 10 ml CH₂Cl₂) drop wise at constant temperature of −60° C. After 15 min of stirring 4-phenyl butanol (3.06 ml, 20.4 mmol) in CH₂Cl₂ (5 ml) was added over 5 min. After an additional 30 min, the mixture was quenched by the addition of TEA (13 ml, 93 mmol) followed by stirring for 15 min. The mixture was diluted with ether, washed with water, dried, filtered and concentrated. Purification by flash chromatography on silica gel (CH₂Cl₂ as elutant) gave 2A as a colorless oil (2.2 g, 71%).

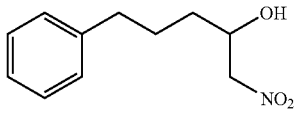

2B

To a solution of 2B (2 g, 13.8 mmol) and nitromethane (2.25 ml, 41 mmol) in THF (30 ml) and t-butanol (30 ml) at r.t. was added potassium-t-butoxide (150 mg, 1.3 mmol) and the mixture was stirred overnight. The solution was quenched with aqueous saturated ammonium chloride and extracted with EtOAc. The extracts were dried, filtered and concentrated. Purification by flash chromatography on silica gel (1:99 ether/CH2Cl2 as elutant) gave 2B as a colorless oil (2.5 g, 88%).

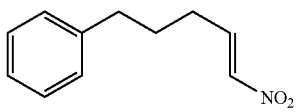

2C

To a stirred solution of 2B (2.5 g, 12 mmol) in 50 ml CH$_2$Cl$_2$ at r.t. was added mesyl chloride (0.93 ml, 12 mmol) followed by slow addition of TEA (1.7 ml, 12.2 mmol) over 5 min. After stirring for 1 h the mixture was washed with water, dried, filtered and concentrated. Purification by flash chromatography on silica gel (1:1 CH$_2$Cl$_2$/hexane as eluting) gave 2C as a colorless oil (1.9 g, 82%).

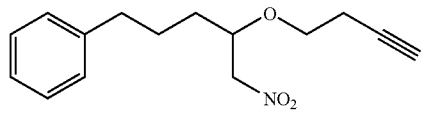

2D

To a slurry of NaH (1.2 g, 50 mmol, 60% dispersion in mineral oil) in THF (30 ml) at r.t. was added 3-butyn-1-ol (2.1 g, 30 mmol) in THF (5 ml) over 10 min. After 1 h of stirring a solution of 2C (1.9 g, 9.8 mmol) in THF (5 ml) at −40° C. was added and the mixture was stirred for 3 h with warming to 0° C. The solution was quenched with aqueous saturated ammonium chloride and extracted with EtOAc. The extracts were dried, filtered and concentrated. Purification by flash chromatography on silica gel (1:7 EtOAc/hexane/as elutant) gave 2D as a colorless oil (1.8 g, 70%).

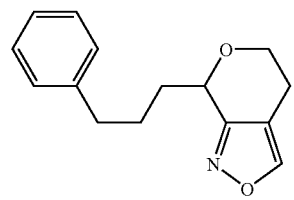

2E

To a stirred solution of 2D (1.7 g, 6.7 mmol) in toluene (35 ml) at r.t. was added phenyl isocyanate (3.6 ml, 33.5 mmol) and TEA (0.1 ml, 0.72 mmol). The mixture was stirred for 24 h resulting in the formation of a precipitate. Water (1.5 ml) was added followed by stirring for 2 h. The solution was filtered to give a yellow oil. Purification by flash chromatography on silica gel (1:2 EtOAc/hexane as elutant) gave 2E as a colorless oil (990 mg, 61%).

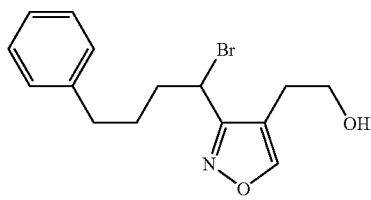

2F

To a stirred solution of 2E (990 mg, 4.05 mmol) in CH$_2$Cl$_2$ at 0° C., was added boron tribromide (8.2 ml, 1M in CH$_2$Cl$_2$). After stirring for 1 h at r.t. the mixture was poured over ice and extracted with ether. The extracts were dried, filtered and concentrated. Purification by flash chromatography on silica gel (1:2 EtOAc/hexane as elutant) gave 2F as a brown oil (690 mg, 53%).

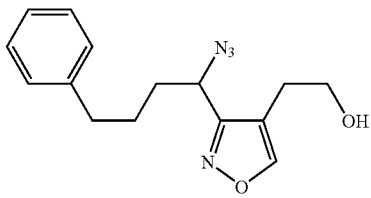

2G

To a stirred solution of 2F (690 mg, 2.1 mmol) in acetone (10 ml) was added sodium azide (1.3 ml in 5 ml water). The mixture was stirred at 55° C. for 1 h, cooled to r.t. The solution was extracted with EtOAc. The extracts were dried, filtered and concentrated to give 2G as an oil (612 mg, 100%).

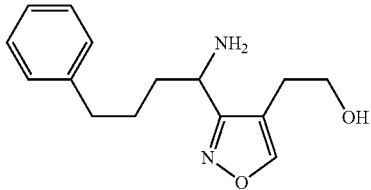

2H

A solution of 2G (610 mg, 2.13 mmol) and triphenylphosphine (600 mg, 2.3 mmol) in THF (20 ml) and water (0.5 ml) was refluxed for 1 h. The mixture was cooled and then concentrated. Purification by flash chromatography on silica gel (13:87 MeOH/CH$_2$Cl$_2$ as elutant) gave 2H as a colorless oil (300 mg, 54%).

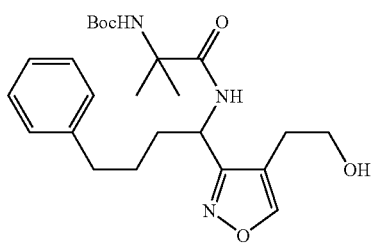

2I 2I was prepared using the method described in 1I substituting 1H with 2H (295 mg, 1.13 mmol) and Boc-2-aminoisobutyric acid (344 mg, 1.7 mmol). 2I was obtained as a colorless oil (430 mg, 85%).

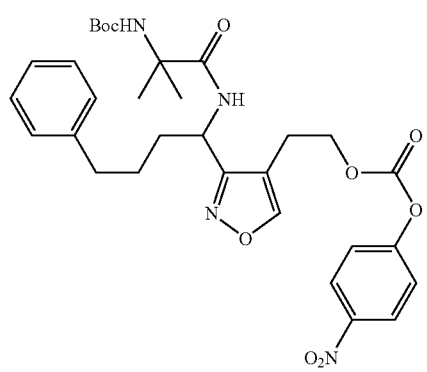

2J 2J was prepared using the method described in 1K substituting 1J with 2I (307 mg, 0.690 mmol) and 4-nitrophenyl chloroformate (307 mg, 1.5 mmol). 2J was obtained as a colorless oil (420 mg, 99%).

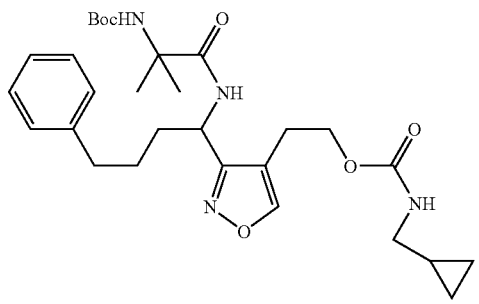

2K 2K was prepared using the method described in 1L substituting 1K with 2J (205 mg, 0.34 mmol) and cyclopropanemethyl amine (45 ul, 0.5 mmol). 2K was obtained as a colorless oil (148 mg, 81%).

Example 2

Example 2 was prepared using the method described in Example 1 substituting 1L with 2K (71.3 mg, 0.134 mmol). The title compound was obtained as a white foam (61.5 mg, 98%). MS (M+H) is 443; HPLC retention time 3.71 min.

Example 3

(4-Hydroxy-butyl)-carbamic acid 2-{3-[1-(2-amino-2-methyl-propionylamino)-4-phenyl-butyl]-isoxazol-4-yl}-ethyl ester

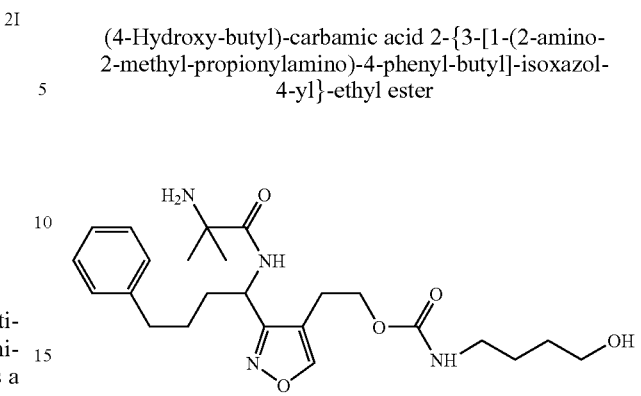

3A was prepared using the method described in 1L substituting 1K with 2J (205 mg, 0.34 mmol) and cyclopropanemethyl amine with 4-amino-1-butanol (45 µl, 0.51 mmol). 3A was obtained as a colorless oil (150 mg, 80%).

Example 3

Example 3 was prepared using the method described in Example 1 substituting 1L with 3A (76 mg, 0.134 mmol). The title compound was obtained as a white foam (65 mg, 98%). MS (M+H) is 461; HPLC retention time 3.07 min

Example 4

(3-Hydroxy-propyl)-carbamic acid 2-{5-[1-(2-amino-2-methyl-propionylamino)-4-phenyl-butyl]-[1,2,4]triazol-1-yl}-ethyl ester

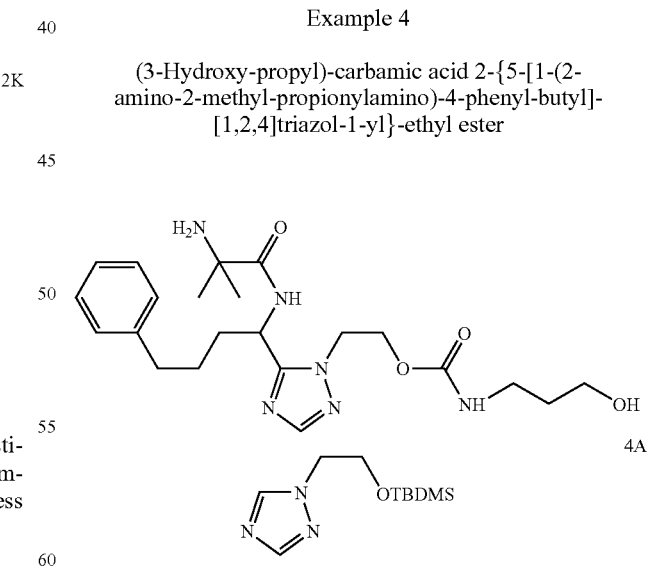

To a stirred solution of triazole (0.76 mg, 11 mmol) in THF (30 ml) at 0° C. was added (2-bromo-ethoxy)-t-butyl-dimethylsilane (2.4 g, 10 mmol) and DBU (1.83 g, 12 mmol) slowly over 1 h. The mixture was stirred at r.t. for 48 h, then filtered and concentrated. Purification by flash chromatography on silica gel (1:2 EtOAc/hexane as elutant) gave 4A (2 g, 88%).

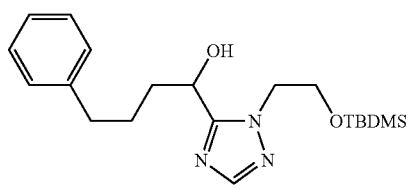
4B

To a stirred solution of 4A (1.4 g, 6.2 mmol) in THF (25 ml) at −78° C. was added nBuLi (2.5 ml, 2.5M in hexane) drop wise. After the mixture is stirred for 1 hr, 4-phenyl-butyryl-adehyde (1g, 6.83 mmol) in 10 ml ether was added rapidly. The mixture is stirred at −78° C. for 20 min and for 3 h at r.t. The solution was quenched and extracted with EtOAc. The extracts were dried, filtered and concentrated. Purification by flash chromatography on silica gel (2:10 EtOAc/hexane as elutant) gave 4B (1.5 g, 65%).

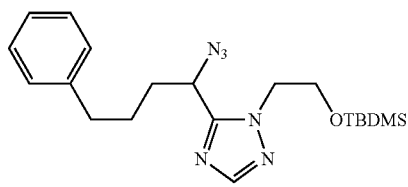
4C

To a solution of 4B (1.45 g, 3.88 mmol) and diphenyl-phosphoryl azide (1.3 g, 4.65 mmol) in toluene (15 ml) at 0° C. was added DBU (0.71 g, 4.65 mmol). The mixture was stirred at r.t. for 24 h, quenched and extracted with EtOAc. The extracts were dried, filtered and concentrated. Purification by flash chromatography on silica gel (1:10 EtOAc/hexane as elutant) gave 4C (350 mg, 24%).

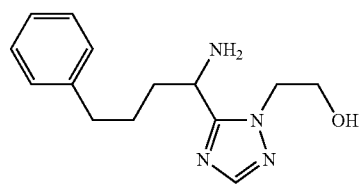
4D

To 4C (345 mg, 0.86 mmol) in EtOH (15 ml) was added Pd—C catalyst (50 mg, 5% Pd by weight) and stirred at r.t. with a hydrogen balloon for 3 h. The catalyst was filtered and concentrated. The residue was dissolved in CH$_2$Cl$_2$ (5 ml) and HCl (3 ml) in dioxane (4N) was added. After stirring for 5 hrs, the mixture was concentrated and dried to give 4D.

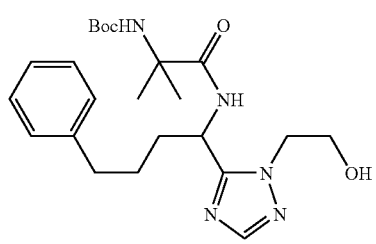
4E

A solution of 4D (0.86 mmol) in CH$_2$Cl$_2$ (3 ml) & N,N-diisopropylethylamine (1.5 ml, 8.6 mmol) was stirred for 5 min and Boc-2-aminoisobutyric acid (175 mg, 0.86 mmol), 1-hydroxy-7-azabenzotriazole (176 mg, 1.3 mmol) and EDAC (250 mg, 1.3 mmol) was added. After stirring overnight the mixture was quenched, extracted with CH$_2$Cl$_2$, dried, filtered and concentrated. The residue was dissolved in THF (2 ml) and MeOH (0.5 ml), then treated with LiOH (0.86 ml, aq. 4N). The mixture was stirred at r.t. for 3 h and then concentrated. Purification by flash chromatography on silica gel (1:4 EtOAc/hexane as elutant) gave 4E (190 mg, 75%).

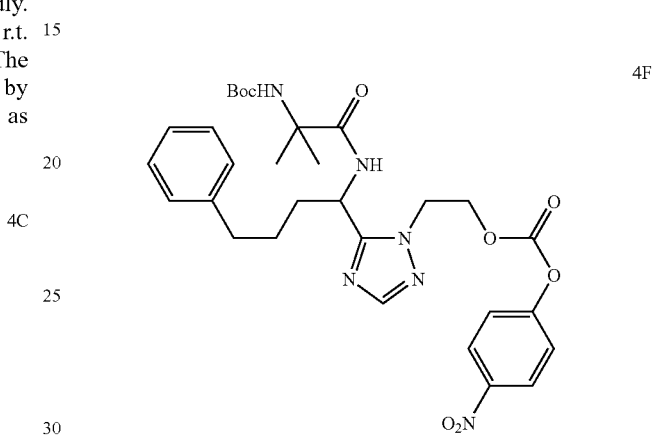
4F 4F was prepared using the method described in 1K substituting 1J with 4E (170 mg, 0.38 mmol) and 4-nitrophenyl chloroformate (154 mg, 0.76 mmol). 4F was obtained as a colorless oil (219 mg, 93%).

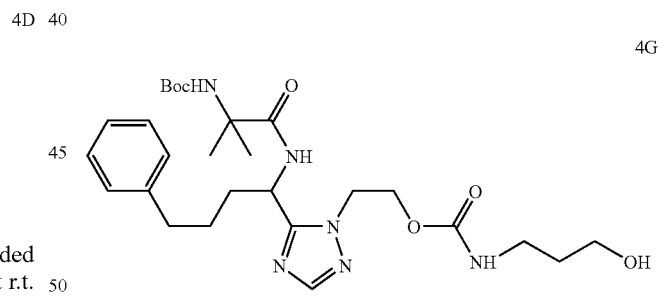
4G 4G was prepared using the method described in 1L substituting 1K with 4F (70 mg, 0.1 mmol) and cyclopropanemethyl amine with 4-amino-butan-1-ol (17 mg, 0.2 mmol). 4G was obtained as a colorless oil (16 mg).

Example 4

Example 4 was prepared using the method described in Example 1 substituting 1L with 4G (16 mg). The title compound was obtained as a white foam (30 mg, 57%). MS (M+H) is 461; HPLC retention time 2.7 min

Example 5

3-Hydroxy-pyrrolidine-1-carboxylic acid 2-{5-[1-(2-amino-2-methyl-propionylamino)-4-phenyl-butyl]-[1,2,4]triazol-1-yl}-ethyl ester

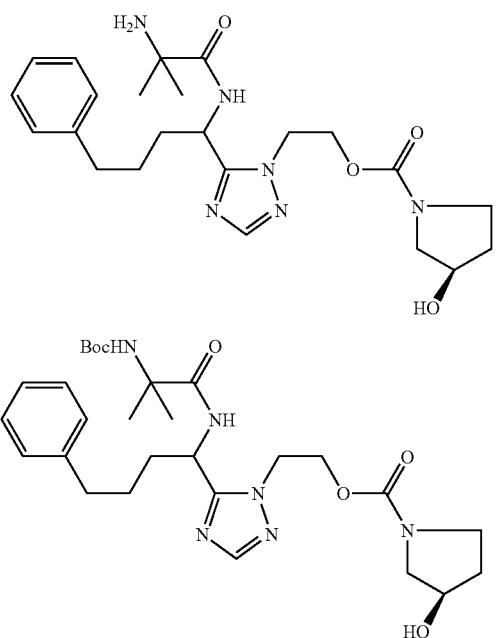

5A was prepared using the method described in 1L substituting 1K with 4F (70 mg, 0.1 mmol) and cyclopropanemethyl amine with pyrrolidin-3-ol (17 mg, 0.2 mmol). 5A was obtained as a colorless oil.

Example 5

Example 5 was prepared using the method described in Example 1 substituting 1L with 5A. The title compound was obtained as a white foam (43 mg, 82%). MS (M+H) is 459; HPLC retention time 2.7 min

Example 6

3-Acetylamino-pyrrolidine-1-carboxylic acid 2-{5-[1-(2-amino-2-methyl-propionylamino)-4-phenyl-butyl]-[1,2,4]triazol-1-yl}-ethyl ester

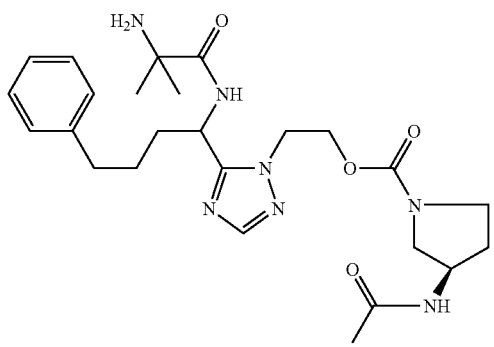

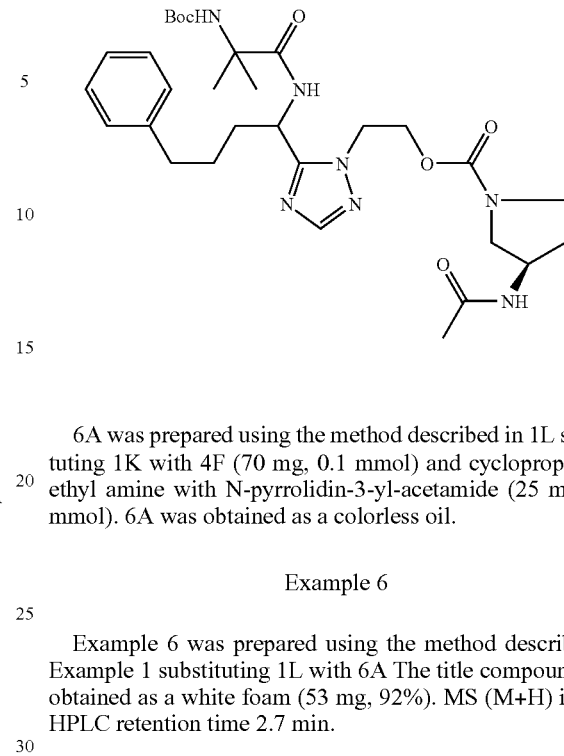

6A was prepared using the method described in 1L substituting 1K with 4F (70 mg, 0.1 mmol) and cyclopropanemethyl amine with N-pyrrolidin-3-yl-acetamide (25 mg, 0.2 mmol). 6A was obtained as a colorless oil.

Example 6

Example 6 was prepared using the method described in Example 1 substituting 1L with 6A The title compound was obtained as a white foam (53 mg, 92%). MS (M+H) is 500; HPLC retention time 2.7 min.

Example 7

(4-Hydroxy-butyl)-carbamic acid 2-{5-[1-(2-amino-2-methyl-propionylamino)-4-(2-bromo-phenyl)-butyl]-[1,2,4]triazol-1-yl}-ethyl ester

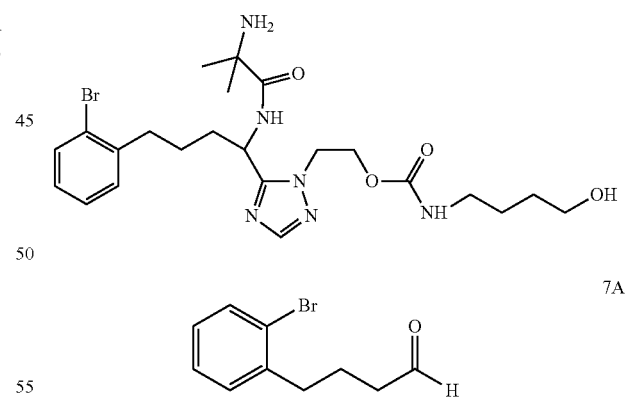

To a stirred solution of 1-bromo-2-iodo-benzene (20 g, 71 mmol) in DMF (70 ml) was added but-3-ene-1-ol (7.65 g, 106 mmol), palladium acetate (0.32 g, 1.4 mmol), tert-butyl ammonium chloride (19.7 g, 71 mmol) and NaHCO₃ (15 g, 176.8 mmol). The mixture was heated at 40° C. for 24 h and filtered. The residue was dissolved in water (50 ml) and extracted with CH₂Cl₂, dried, filtered and concentrated. Purification by flash chromatography on silica gel (1:6 EtOAc/hexane as elutant) gave 7A (13.6 g, 84%).

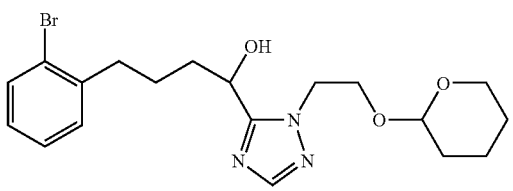
7B

To a stirred solution of 1-[(2-tetrahydro-pyran-2-yloxy)-ethyl-1H-[1,2,4]-triazole (1.9 g, 10 mmol) in THF (20 ml) at −78° C. was added nBuLi (4 ml, 10 mmol, 2.5M in hexane) drop wise. After the mixture is stirred at −78° C. for 30 min and at 0° C. for 30 min, it is recooled to −78° C. and 7A (2.26 g, 10 mmol) in THF (20 ml) was added rapidly. The mixture is stirred at −78° C. for 10 min, 70° C. for 10 min and for 20 min at r.t. The solution was quenched and extracted with EtOAc. The extracts were dried, filtered and concentrated. Purification by flash chromatography on silica gel (1:20 EtOAc/hexane as elutant) gave 7B (1.6 g, 77%).

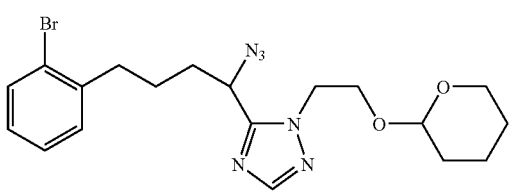
7C 7C was prepared using the method described in 4C substituting 4B with 7B (1.6 g, 3.9 mmol) and diphenylphosphoryl azide (1.3 g, 4.7 mmol). 7C was obtained as a colorless oil (1.2 g, 69%).

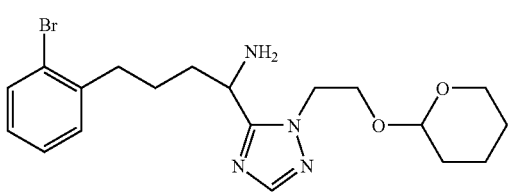
7D

To a solution of 7C (4.4 g, 9.8 mmol) in THF (50 ml) at 0° C. was added lithium aluminum hydride (10.3 ml, 10.3 mmol, 1M in THF). After stirring the mixture for 1.5 h at 0° C., it was quenched with 1N NaOH (~10 ml) and extracted with ether. The extracts were dried, filtered and concentrated. The residue was co-evaporated with MeOH:toluene:CH₂Cl₂ (1:1:1) to provide 7D (4.9 g, <99%).

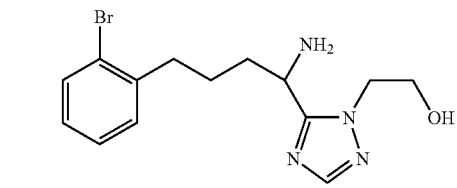
7E

A solution of 7D (3.3 g, 7.8 mmol) in MeOH (20 ml) and HCl (10 ml, 4M in dioxane) was stirred for 1 h and then concentrated. The residue was co-evaporated with MeOH:toluene (1:1) to provide 7E (3.1 g, <99%).

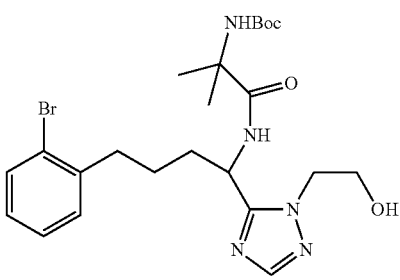
7F 7F was prepared using the method described in 4E substituting 4D with 7E (3.1 g, 9.3 mmol) and Boc-2-aminoisobutyric acid (1.9 g, 9.7 mmol). 7F was obtained as a colorless oil (2.3 g, 67%).

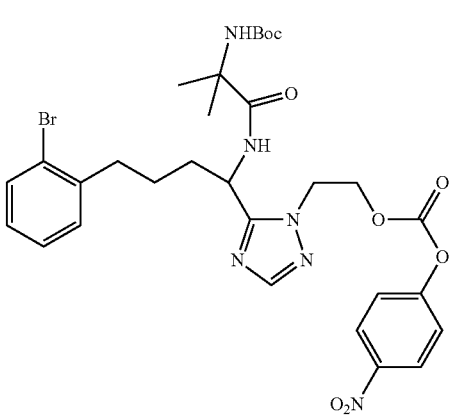
7G 7G was prepared using the method described in 1K substituting 1J with 7F (260 mg, 0.5 mmol) and 4-nitrophenyl chloroformate (201 mg, 1.0 mmol). 7G was obtained as a colorless oil (298 mg, 86%).

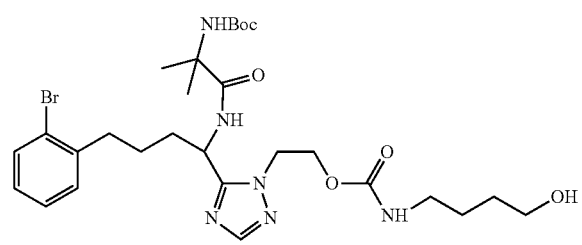
7H 7H was prepared using the method described in 1L substituting 1K with 7G (70 mg, 0.1 mmol) and cyclopropanemethyl amine with 4-amino-butan-1-ol (17 mg, 0.2 mmol). 7H was obtained as a colorless oil.

Example 7

Example 7 was prepared using the method described in Example 1 substituting 1L with 7H. The title compound was obtained as a white foam (30 mg, 57%). MS (M+H) is 540; HPLC retention time 3.06 min.

Example 8

Cyclopropylmethyl-carbamic acid 2-{5-[1-(2-amino-2-methyl-propionylamino)-4-(2-bromo-phenyl)-butyl]-[1,2,4]triazol-1-yl}-ethyl ester

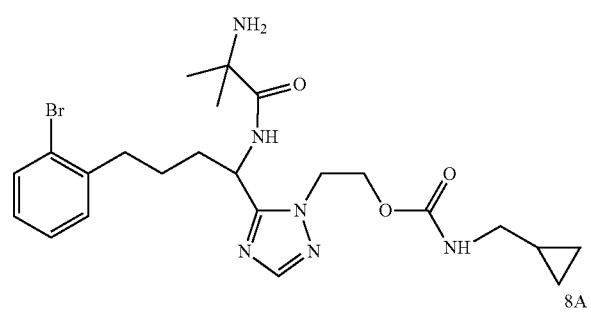

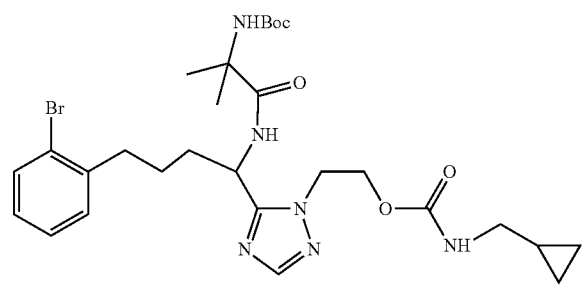

8A was prepared using the method described in 1L substituting 1K with 7G (74 mg, 0.1 mmol) and cyclopropanemethyl amine (15.2 mg, 0.21 mmol). 8A was obtained as a colorless oil.

Example 8

Example 8 was prepared using the method described in Example 1 substituting 1L with 8A. The title compound was obtained as a white foam (31.6 mg, 58%). MS (M+H) is 522; HPLC retention time 3.44 min.

Example 9

(3,3,3-Trifluoro-propyl)-carbamic acid 2-{5-[1-(2-amino-2-methyl-propionylamino)-4-(2-bromo-phenyl)-butyl]-[1,2,4]triazol-1-yl}-ethyl ester

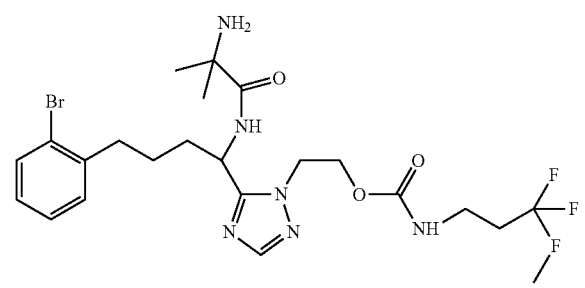

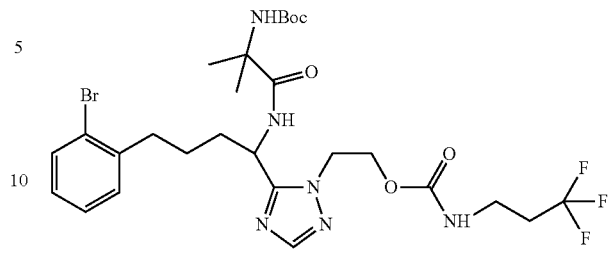

9A was prepared using the method described in 1L substituting 1K with 7G (50 mg, 0.07 mmol) and cyclopropanemethylamine with 3,3,3-trifluoropropylamine (12 mg, 0.08 mmol). 9A was obtained as a colorless oil.

Example 9

Example 9 was prepared using the method described in Example 1 substituting 1L with 9A. The title compound was obtained as a white foam (25 mg). MS (M+H) is 564; HPLC retention time 3.3 min.

Example 10

Cyclopropylmethyl-carbamic acid 2-{5-[1-(2-amino-2-methyl-propionylamino)-4,4-difluoro-4-phenyl-butyl]-[1,2,4]triazol-1-yl}-ethyl ester

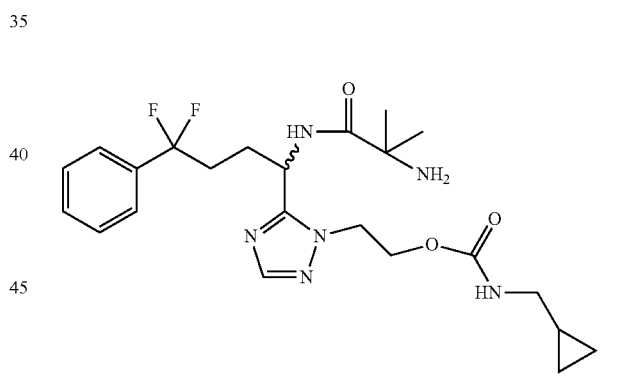

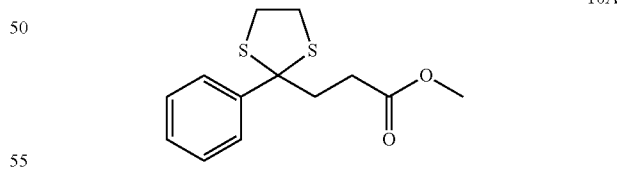

To a stirred solution of methyl-3-benzoyl propionate (9.6 g, 50 mmol) in $CH_2Cl_2$ (200 ml) at 0° C. was added ethan-1,2-dithiol (9.4 g, 100 mmol) and boron trifluoride diethyletherate (3.15 ml, 25 mmol). The mixture was stirred at 0° C. for 4 h and then warmed to r.t. overnight. The solution was concentrated and the residue was treated with NaOH (30 ml). The mixture was extracted with $CH_2Cl_2$, washed with water, brine, dried, filtered and concentrated. Purification by flash chromatography on silica gel (1:10 EtOAc/hexane as eluant) gave 10A (8.85 g, 66%).

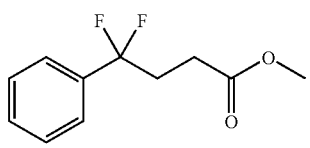
10B

To a solution of nitrosonium tetrafluoroborate (2.4 g, 20.5 mmol) and hydrogen fluoride-pyridine (11.0 ml) in CH$_2$Cl$_2$ (30 ml) at 0° C. in a Teflon bottle was added 10A (2.5 g, 9.33 mmol) drop wise. After stirring for 1 h at 0° C., the mixture was warmed to r.t. and stirred for 1 h. The solution was diluted with CH$_2$Cl$_2$ (100 ml) and then quenched with NaOH (1N aqueous solution), extracted with CH$_2$Cl$_2$, washed with water, brine, dried, filtered and concentrated. Purification by flash chromatography on silica gel (1:10 EtOAc/hexane as eluant) gave 10B (5.2 g, 73%).

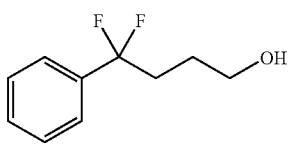
10C

To a solution of 10B (3 g, 14 mmol) in 4:1 THF/MeOH (25 ml) was added lithium borohydride (10.5 ml, 28 mmol, 2M in THF) at r.t. After 3 h of stirring the solution was quenched with aqueous saturated ammonium chloride and then extracted with ether, dried, filtered and concentrated. Purification by flash chromatography on silica gel (1:2 EtOAc/hexane as eluant) gave 10C (2.45 g, 94%).

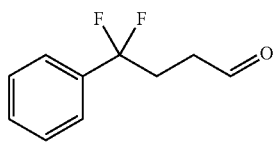
10D

To a solution of 10C (1.2 g, 6.5 mmol) in CH$_2$Cl$_2$ (20 ml) was added florisil (3 g) followed by pyridinium chlorochromate (2.8 g, 12.9 mmol). After stirring for 3 h at r.t. the solution was filtered through celite and concentrated. Purification by flash chromatography on silica gel (1:4 ether/hexane as eluant) gave 10D (0.8 g, 67%).

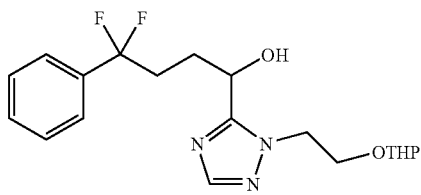
10E 10E was prepared using the method described in 7B substituting 7A with 10D (18.5 ml, 9.25 mmol) and 1-[(2-tetrahydro-pyran-2-yloxy)-ethyl-1H-[1,2,4]-triazole (1.83 g, 9.25 mmol). 10E was obtained as a colorless oil (3.2 g, 90%).

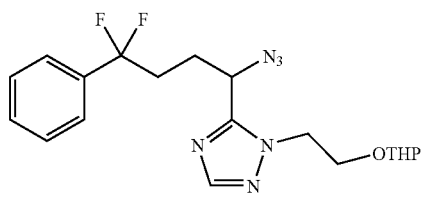
10F 10F was prepared using the method described in 4C substituting 4B with 10E (3.16 g, 8.3 mmol) and diphenylphosphoryl azide (2.7 g, 10 mmol). 10F was obtained as a colorless oil (3.1 g, 93%).

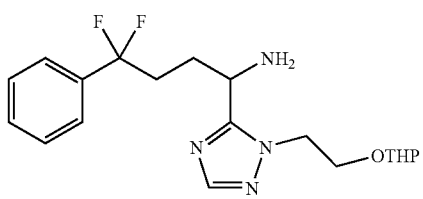
10G 10G was prepared using the method described in 4D substituting 4C with 10F (200 mg, 0.5 mmol) and Pd—C catalyst (50 mg, 5% Pd by weight). 10G was obtained as a salt (185 mg, 82%).

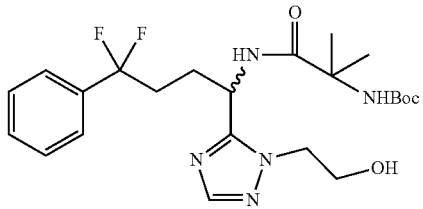
10H 10H was prepared using the method described in 4E substituting 4D with 10G (185 mg, 0.56 mmol) and Boc-2-aminoisobutyric acid (136 g, 0.67 mmol). 10H was obtained as a colorless oil.

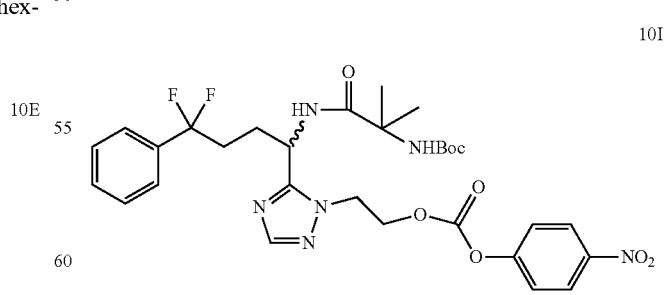
10I 10I was prepared using the method described in 1K substituting 1J with 10H (2.65 g, 5.5 mmol) and 4-nitrophenyl chloroformate (2.21 g, 11.0 mmol). 10I was obtained as a colorless oil (2.2 g, 62%).

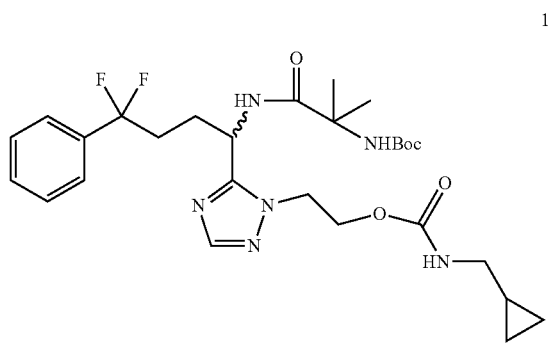

10J 10J was prepared using the method described in 1L substituting 1K with 10I (120 mg, 0.18 mmol) and cyclopropanemethyl amine (15.8 mg, 0.22 mmol). 10J was obtained as a colorless oil.

Example 10

Example 10 was prepared using the method described in Example 1 substituting 1L with 10J. The title compound was obtained as a salt (46 mg). MS (M+H) is 479; HPLC retention time 3.2 min.

Example 11

(R)-(4-Hydroxy-butyl)-carbamic acid 2-{5-[1-(2-amino-2-methyl-propionylamino)-4,4-difluoro-4-phenyl-butyl]-[1,2,4]triazol-1-yl}-ethyl ester

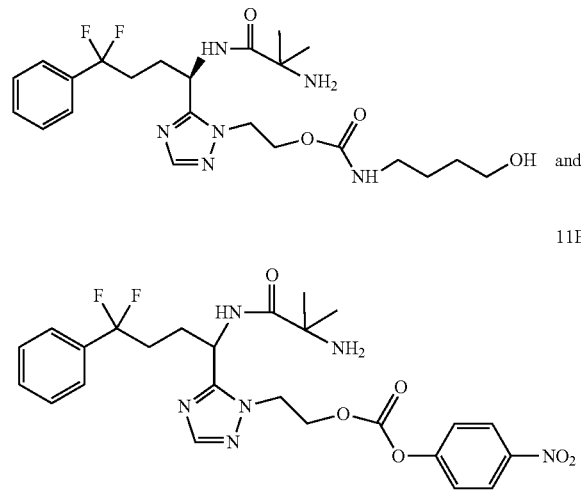

11A

11B 10I was subjected to chiral separation using chiral prep HPLC (Chiralpak AD 5 cm×50 cm 2 µm) and 35% IPA/hexane as elutant) to give 550 mg of 11A (rt=6.54 min)) & 520 mg of 11B (rt=12.85 min).

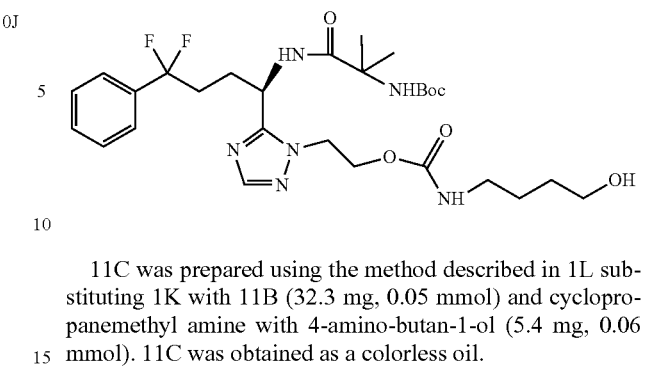

10J 11C was prepared using the method described in 1L substituting 1K with 11B (32.3 mg, 0.05 mmol) and cyclopropanemethyl amine with 4-amino-butan-1-ol (5.4 mg, 0.06 mmol). 11C was obtained as a colorless oil.

Example 11

Example 11 was prepared using the method described in Example 1 substituting 1L with 11C. The title compound was obtained as a salt (35 mg). MS (M+H) is 497; HPLC retention time 2.76 min.

Example 12

(R)-(3,3,3-Trifluoro-propyl)-carbamic acid 2-{5-[1-(2-amino-2-methyl-propionylamino)-4,4-difluoro-4-phenyl-butyl]-[1,2,4]triazol-1-yl}-ethyl ester

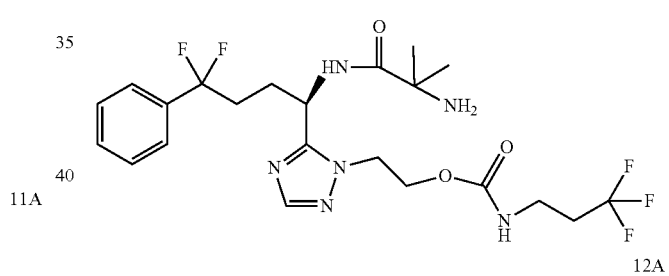

12A

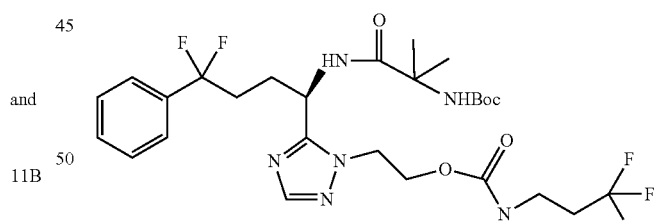

12A was prepared using the method described in 1L substituting 1K with 11B (50 mg, 0.077 mmol) and cyclopropanemethylamine with 3,3,3-trifluoropropylamine (12.8 mg, 0.085 mmol). 12A was obtained as a colorless oil.

Example 12

Example 12 was prepared using the method described in Example 1 substituting 1L with 12A. The title compound was obtained as a salt (22 mg). MS (M+H) is 521; HPLC retention time 3.11 min.

Example 13

(R)-3-Fluoro-pyrrolidine-1-carboxylic acid 2-{5-[1-(2-amino-2-methyl-propionylamino)-4,4-difluoro-4-phenyl-butyl]-[1,2,4]triazol-1-yl}-ethyl ester

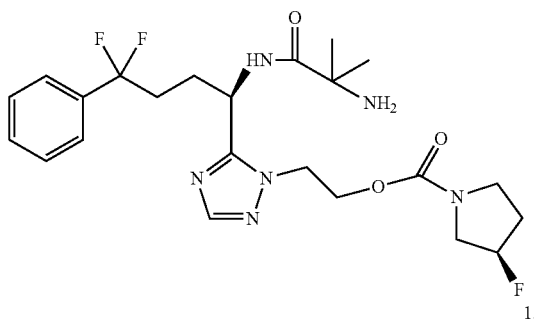

13A

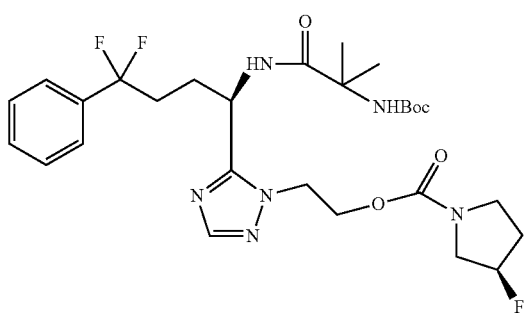

13A was prepared using the method described in 1L substituting 1K with 11B (90 mg, 0.14 mmol) and cyclopropanemethyl amine with 3-fluoro pyrrolidine (1 ml of 0.14M in MeOH, 0.14 mmol). 13A was obtained as a colorless oil.

Example 13

Example 13 was prepared using the method described in Example 1 substituting 1L with 13A. The title compound was obtained as a salt (57 mg). MS (M+H) is 497; HPLC retention time 3.06 min.

Example 14

(S)-3-Fluoro-pyrrolidine-1-carboxylic acid 2-{5-[1-(2-amino-2-methyl-propionylamino)-4,4-difluoro-4-phenyl-butyl]-[1,2,4]triazol-1-yl}-ethyl ester

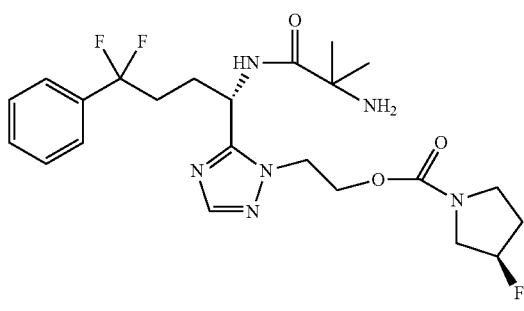

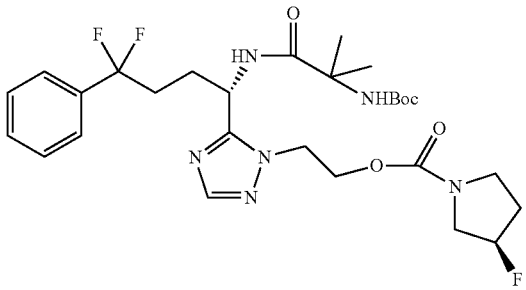

14A 14A was prepared using the method described in 1L substituting 1K with 11A (90 mg, 0.14 mmol) and cyclopropanemethyl amine with 3-fluoro pyrrolidine (1 ml of 0.14M in MeOH, 0.14 mmol). 14A was obtained as a colorless oil.

Example 14

Example 14 was prepared using the method described in Example 1 substituting 1L with 14A. The title compound was obtained as a salt (57 mg). MS (M+H) is 497; HPLC retention time 3.06 min.

Example 15

(R)-2-Amino-N-{1-[4-(2-cyano-ethyl)-isoxazol-3-yl]-2-phenoxy-ethyl}-2-methyl-propionamide

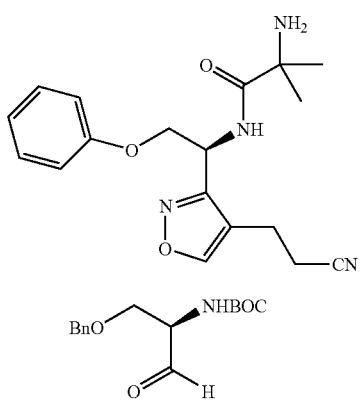

15A

To a stirred solution of oxalyl chloride (1.4 ml, 14.9 mmol) in $CH_2Cl_2$ (19 ml) −78° C. was added DMSO (2.3 ml, 32.4 mmol) slowly. After the mixture is stirred for 15 min, a solution of (2-benzyloxy-1-hydroxymethyl-ethyl)-carbamic acid tert-butyl ester (2.11 g, 7.5 mmol) in $CH_2Cl_2$ (19 ml) was added slowly and the reaction was stirred for 1 h. Then TEA (4.2 ml, 30 mmol) was added and stirred for 15 min followed by stirring for 1.5 h after warming to r.t. The solution was quenched with cold 0.5M potassium hydrogen phosphate (70 ml) and then extracted with $CH_2Cl_2$, washed with 5% aqueous $NaHCO_3$, dried, filtered and concentrated. Purification by flash chromatography on silica gel (3:7 EtOAc/hexane as eluant) gave 15A (2.1 g, <99%).

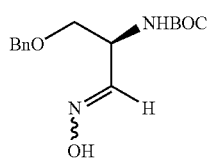

15B

To 15A (2.1 g, 7.5 mmol) in pyridine (80 ml) was added hydroxylamine hydrochloride (1.06 g, 14.9 mmol) and stirred for 13 h at r.t. The solution was diluted with CH$_2$Cl$_2$, washed with water, dried, filtered and concentrated. Purification by flash chromatography on silica gel (3:2 EtOAc/hexane as eluant) gave 15B (2.1 g, 93%).

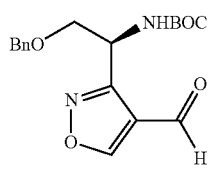

15C

To a solution of 15B (414.3 mg, 1.4 mmol) in chloroform (4.4 ml) was added N-chlorosuccinimide (307 mg, 2.25 mmol) slowly over 30 min followed by stirring at r.t. for 30 min and at 45° C. for 20 min. To the mixture was added 3-dimethylamino-propenal (314 µl, 2.82 mmol) and TEA (217 µl, 1.6 mmol) in chloroform (1.0 ml) slowly while heating at 45° C. The mixture was heated at 45° C. for 1 h and then warmed to r.t. over 4 h. The solution was diluted with EtOAc, washed with 0.5M potassium hydrogen phosphate, 5% aqueous NaHCO$_3$, brine, dried, filtered and concentrated. Purification by flash chromatography on silica gel (85:15 CH$_2$Cl$_2$/ether as eluant) gave 15C (246 mg, 51%).

15D

A solution of 15C (246 mg, 0.71 mmol) and triphenyl phosphanylidene-acetonitrile (266 mg, 0.86 mmol) in CH$_2$Cl$_2$ (30 ml) at r.t. was stirred for 14 h. The solution was concentrated. Purification by flash chromatography on silica gel (3:7 EtOAc/hexane as eluant) gave 15D as a yellow solid (227 mg, 87%).

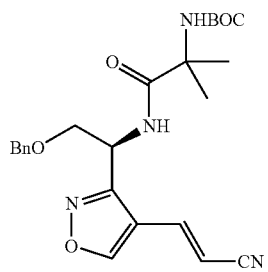

15E

To 15D (227 mg, 0.62) was added 15% TFA/CH$_2$Cl$_2$ (8 ml) and thioanisole (0.22 ml, 1.87 mmol) and the solution was allowed to stand at r.t. for 3 h. The solution was concentrated and co-evaporated with CH$_2$Cl$_2$ and MeOH and concentrated. To the residue in DMF (0.6 ml) and DCE (0.4 ml) at 0° C. was added boc-2-aminoisobutyric acid (189 mg, 0.93 mmol), 1-hydroxy-7-azabenzotriazole (127 mg, 0.93 mmol) & EDAC (170 mg, 0.93 mmol) in DMF (1.1 ml) and DCE (0.6 ml) was added, followed by N,N-diisopropylethylamine (0.27 ml, 1.55 mmol). After stirring the mixture overnight, it was quenched, extracted with EtOAc, washed with aqueous NaHCO$_3$, brine, dried, filtered and concentrated. Purification by flash chromatography on silica gel (7:3 CH$_2$Cl$_2$/ether as elutant) gave a yellow solid 15E (246 mg, 88%).

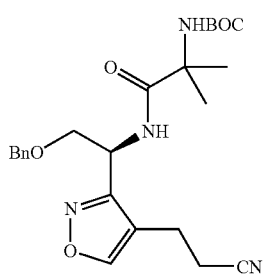

15F

To 15E (143 mg, 0.32 mmol) in 1/1 THF:MeOH (12 ml) was added Pd—C catalyst (80 mg, 5% Pd by weight) and stirred at r.t. with a hydrogen balloon for 1.7 h. The catalyst was filtered and rinsed with MeOH and EtOAc. The filtrates were concentrated to give a colorless oil 15F (132 mg, 92%).

Example 15

A solution of 15F (154 mg, 0.34 mmol) in 10% TFA/CH$_2$Cl$_2$ (5 ml) was stirred for 4 h and then concentrated. The residue was purified by preparative HPLC to give Example 16 and the title compound as a colorless foam (119 mg, 75%). MS (M+H) is 357; HPLC retention time 4.47 min.

Example 16

(R)-2-Amino-N-{2-benzyloxy-1-[4-(2-tert-butylcarbamoyl-ethyl)-isoxazol-3-yl]-ethyl}-2-methyl-propionamide

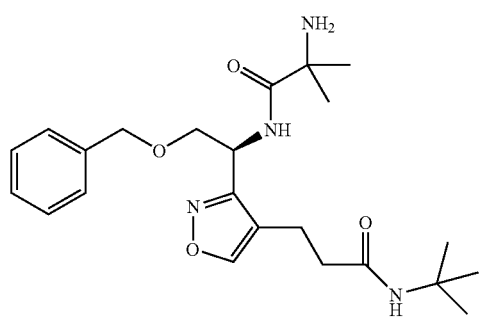

Example 16 was obtained from Example 15 as a yellowish solid (10 mg, 75%). MS (M+H) is 431; HPLC retention time 5.95 min.

Example 17

(R)-Cyclopropylmethyl-carbamic acid 2-[3-[1-(2-amino-2-methyl-propionylamino)-2-benzyloxy-ethyl]-1-(cyclo-propylmethyl-carbamoyl)-5-hydroxy-1H-pyrazol-4-yl]-ethyl ester

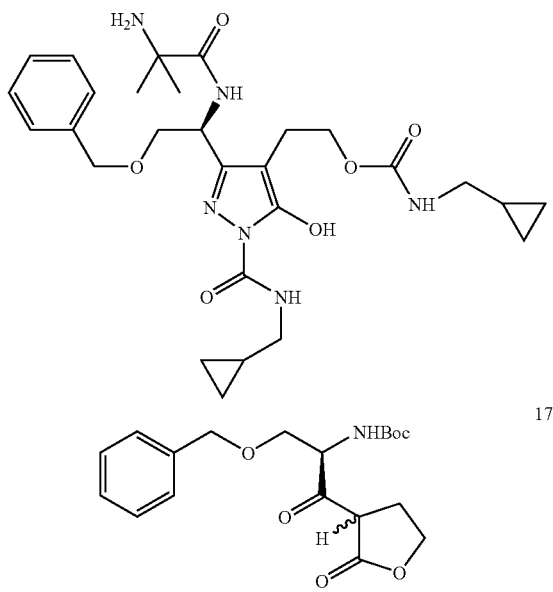

17A

To a stirred solution of LDA (16.0 ml, 32.0 mmol, 2.0M in heptane/THF) at −78° C. under argon was added a solution of γ-butyrolactone (2.75 g, 31.9 mmol) in THF (10 ml) drop wise over 20 min. The light yellow solution was stirred for 30 min. In the meanwhile, a stirred solution of (R)Boc (OBzl)Ser (3.00 g, 10.2 mmol) in THF (40 ml) at room temperature under argon was treated with carbonyl diimidazole (1.74 g, 10.7 mmol) in one portion. The resulting clear solution was stirred for 50 min. This solution was then added drop wise over 30 min to the LDA/butyrolactone mixture prepared above. After 1 h, the reaction mixture was quenched with 10% citric acid at −78° C. and then allowed to warm to room temperature. The mixture was extracted twice with EtOAc. The extracts were combined, dried (Na₂SO₄) and evaporated. Purification by flash chromatography on silica gel (1:20 EtOAc/hexanes) provided 17A as a colorless oil (2.80 g, 77%).

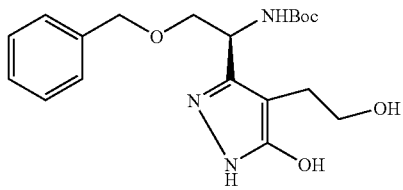

17B

To a stirred solution of 17A (1.81 g, 4.98 mmol) in 1:1 EtOH/water (25 ml) was added hydrazine hydrate (0.30 ml, 6.2 mmol). The mixture was heated to reflux under argon for 24 h. The resulting solution was evaporated and then re-evaporated from toluene to give as an amorphous solid 17B (1.79 g, 99%).

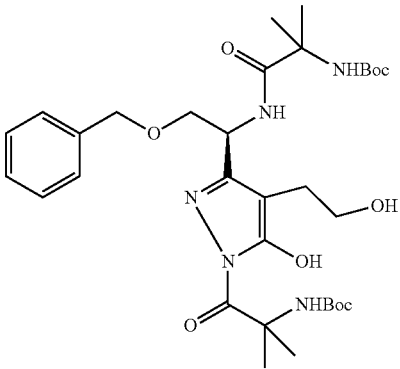

17C

To a solution of CH₂Cl₂ (6 ml) and methanol (4 ml) at 0° C. under argon was added, drop wise, acetyl chloride (2.56 ml, 36.0 mmol) over 5 min. After 1 h, the solution was added to 17B (429 mg, 1.14 mmol) and the reaction warmed to room temperature. After 2 h, the resulting solution was evaporated and then re-evaporated from toluene to give a thick oil. In the meanwhile, a slurry of BocAib (700 mg, 3.44 mmol) and HOAT (470 mg, 3.44 mmol) in 1,2-dichloroethane (10 ml) at room temperature was treated with EDAC (655 mg, 3.44 mmol). After a few minutes, a yellow solution formed. After 1 h, the solution was added to the thick oil prepared above and rapidly agitated as NMM (0.5 ml, 4.5 mmol) was added. After 14 h, the reaction mixture was diluted with EtOAc and washed once with saturated NaHCO₃ solution. The organic extract was dried (MgSO₄), filtered and evaporated. Purification by flash chromatography on silica gel (1:1 EtOAc/CH₂Cl₂) provided 17C as a colorless oil (363 mg, 49%).

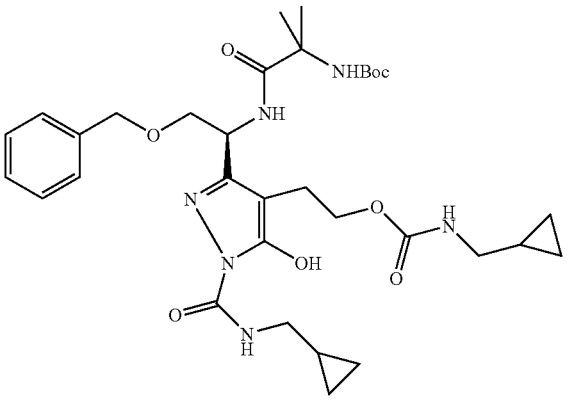

17D

To a stirred solution of 17C (342 mg, 0.528 mmol) in CH₂Cl₂ (3 ml) was added concentrated ammonium hydroxide (2 ml). The resulting mixture was stirred rapidly for 16 h and then extracted three times with CH₂Cl₂. The organic extracts were combined, dried (MgSO₄) and evaporated.

The resulting oil was dissolved in CH₂Cl₂ (3 ml) and cooled to 0° C. The solution was treated with pyridine (86 μl, 1.05 mmol) and then 4-nitrophenyl-chloroformate (215 mg, 1.07 mmol). After 1 h, the reaction was warmed to room temperature and stirred 1 h more. Cyclopropylmethylamine (0.2 ml) was then added and the reaction stirred for 1 h more. After quenching with 10% citric acid solution, the reaction mixture was extracted three times with EtOAc. The extracts were combined, dried (MgSO$_4$) and evaporated. Purification by preparative reverse phase HPLC provided 17D as a colorless oil (112 mg, 34%).

Example 17

To a solution of CH$_2$Cl$_2$ (2 ml) and methanol (1.2 ml) at 0° C. under argon was added, drop wise, acetyl chloride (0.8 ml, 11.3 mmol) over 5 min. After 1 h, the solution was added to 17D (100 mg, 0.152 mmol) and the reaction warmed to room temperature. After 30 min, the resulting solution was evaporated, dissolved in water and lyophilized to give the title compound as its hydrochloride salt as an amorphous off-white solid (77 mg, 85% yield). MS (M+H) is 557; HPLC retention time 3.72 min.

Example 18

(R)-Isobutyl-carbamic acid 2-{3-[1-(2-amino-2-methyl-propionylamino)-2-benzyloxy-ethyl]-5-hydroxy-1-methanesulfonyl-1H-pyrazol-4-yl}-ethyl ester

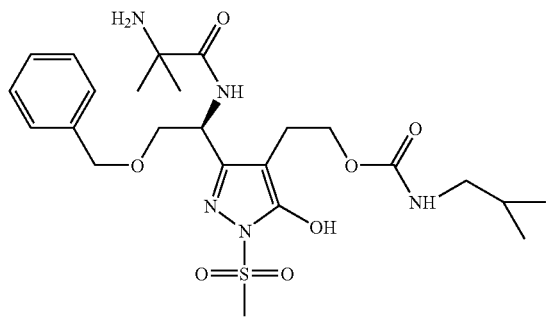

18A

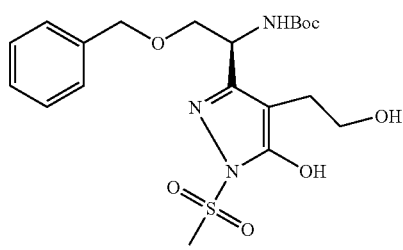

To a stirred solution of 17B (mg, 1.88 mmol) in THF (15 ml) at room temperature was added pyridine (170 µl, 2.10 mmol) and then methanesulfonyl chloride (150 µl, 1.94 mmol). After 2 h, the reaction was diluted with EtOAc and washed once with 2:3 1M hydrochloric acid/brine (5 ml). The organic extract was dried (Na$_2$SO$_4$), filtered and evaporated. Purification by flash chromatography on silica gel (3:5 EtOAc/CH$_2$Cl$_2$) gave 18A as a yellow oil (401 mg, 47%).

18B

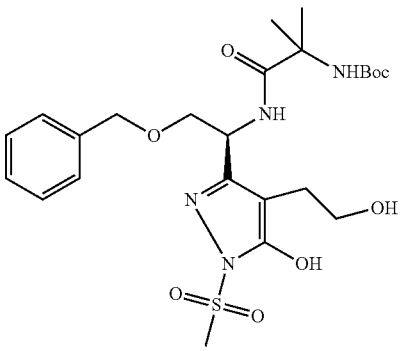

17B (554 mg, 1.22 mmol) was dissolved in HCl/dioxane (4 N, 5 ml, 20 mmol) at room temperature and stirred. After 2 h, the resulting solution was evaporated and then re-evaporated from toluene to give a thick oil. In the meanwhile, a slurry of BocAib (508 mg, 2.5 mmol) and HOAT (343 mg, 2.5 mmol) in 1,2-dichloroethane (10 ml) at room temperature was treated with EDAC (475 mg, 2.5 mmol). After a few minutes, a yellow solution formed. After 1 h, the solution was added to a solution of the thick oil prepared above in dichloromethane (5 ml) and rapidly agitated as NMM (202 µl, 1.83 mmol) was added. After 14 h, the reaction mixture was diluted with EtOAc and washed once with saturated NaHCO$_3$ solution. The organic extract was dried (MgSO$_4$), filtered and evaporated. Purification by flash chromatography on silica gel (3:2 EtOAc/CH$_2$Cl$_2$) provided 18B as a white amorphous solid (403 mg, 75%).

18C

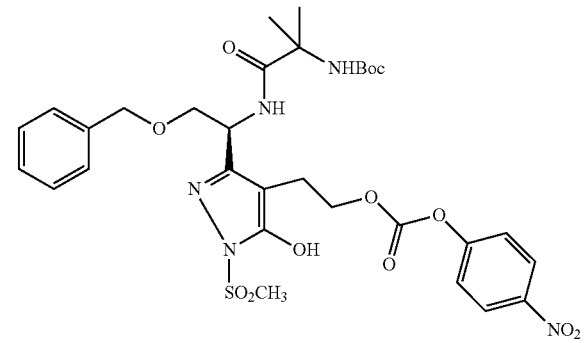

To a stirred solution of 18B (390 mg, 0.722 mmol) in THF (8 ml) at room temperature under argon was added pyridine (131 µl, 1.62 mmol) and then 4-nitrophenyl-chloroformate (148 mg, 0.734 mmol). After 4 h, the reaction mixture was filtered and the filtrate evaporated. Purification by flash chromatography on silica gel (1:3 EtOAc/CH$_2$Cl$_2$) provided 18C as an amorphous white solid (324 mg, 64%).

18D

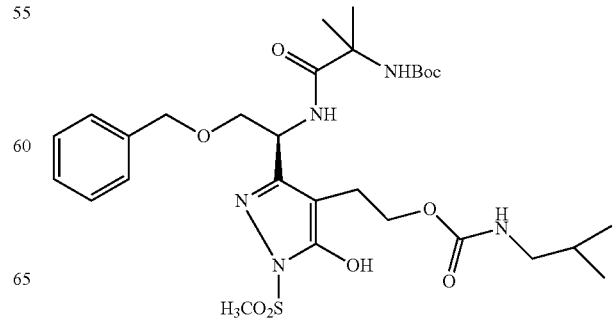

To a stirred solution of 18C compound (320 mg, 0.454 mmol) in THF (2 ml) at room temperature under argon was added isobutylamine (0.2 ml, 2.0 mmol). After 2 h, the reaction mixture was evaporated, redissolved in EtOAc and washed twice with 0.5M NaOH. The organic phase was dried (MgSO₄) and evaporated to give 18D as a clear oil (284 mg, 98%).

Example 18

To a solution of methanol (6 ml) at 0° C. under argon was added, drop wise, acetyl chloride (0.6 ml, 8.5 mmol) over 5 min. After 1 h, the solution was added to 18D (180 mg, 0.28 mmol) and the reaction warmed to room temperature. After 30 min, the resulting solution was evaporated, dissolved in water and lyophilized to give the title compound as its hydrochloride salt as an amorphous off-white solid (148 mg, 91% yield). MS (M+H) is 540; HPLC retention time 3.58 min.

Example 19

(R)2-Amino-N-{2-benzyloxy-1-[5-(3-chloro-phenyl)-[1,3,4]oxadiazol-2-yl]-ethyl}-2-methyl-propionamide

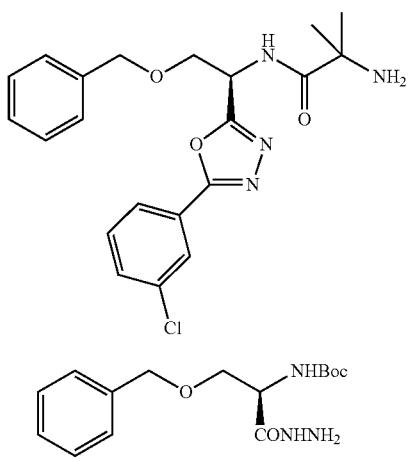

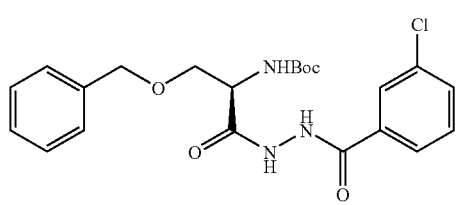
19A

To a solution of 3-benzyloxy-2-tert-butoxycarbonylamino-propionic acid (1.5 g, 5 mmol) in THF (10 ml) at r.t was added 1,1'-carbonyldiimidazole (810 mg, 5 mmol). The resulting slurry was stirred for 1 h followed by addition of anhydrous hydrazine (0.17 ml, 5.5 mmol). After 1 h the yellowish slurry was diluted with water and then extracted with EtOAc, dried, filtered and concentrated to give 19A (2.06 g, <99%).

19B

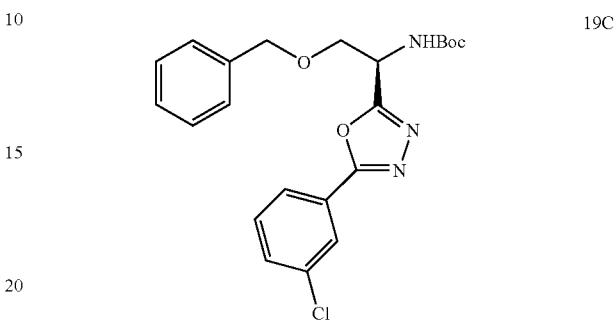

To a stirred solution of 19A (0.7 mg, ~1.7 mmol) in CH₂Cl₂ at 0° C. was added TEA (0.3 ml, 2.1 mmol) followed by 3-chlorobenzoyl chloride (0.25 ml, 1.9 mmol) drop wise. The mixture was stirred for 20 min and then warmed to rt. After 2 h the reaction mixture was diluted with EtOAc, washed with aqueous saturated NaHCO3, 10% citric acid and brine, dried, filtered and concentrated. Purification by flash chromatography on silica gel (2:3 EtOAc/hexane as eluant) gave 19B (590 mg, 77%).

19C

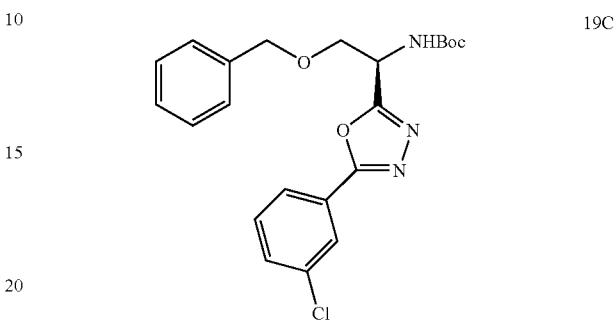

To a stirred slurry of 19B (590 mg, 1.3 mmol) and 1,2-dibromo-1,1,2,2-tetrachloroethane (940 mg, 2.9 mmol) in acetonitrile at 0° C. was added triphenylphosphine (760 mg, 2.9 mmol). Then TEA (0.8 ml, 5.8 mmol) was added over 1 min. After 30 min the yellow slurry formed was warmed to rt. After additional 2 h of stirring the red solution formed was concentrated. The residue was dissolved in EtOAc filtered and washed the filtrate with brine, dried, filtered and concentrated. Purification by flash chromatography on silica gel (1:10 Ether/CH₂Cl₂ as eluant) gave 19C (370 mg, 66%).

19D

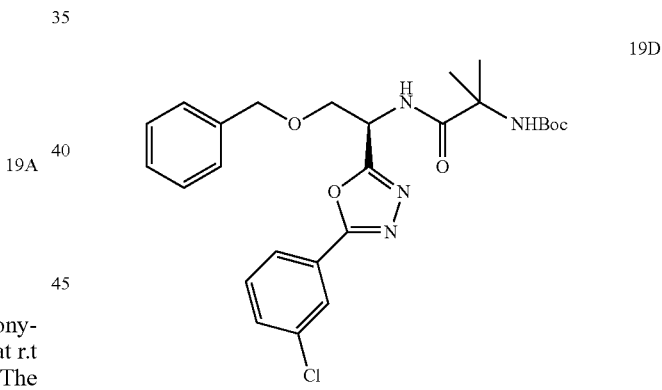

A stirred solution of 19C (370 mg, 0.72 mmol) in CH₂Cl₂ (3 ml) was treated with 0.8 ml of TFA for 3 h. The mixture was then concentrated. The residue in CH₂Cl₂ was added to a stirred solution of Boc-2-aminoisobutyric acid (220 mg, 1.1 mmol), 1-hydroxy-7-azabenzotriazole (1486 mg, 1.1 mmol) and EDAC (205 mg, 1.1 mmol). Then NMM (0.4 ml, 3.2 mmol) was added. After stirring for 15 h the mixture was quenched, extracted with EtOAc, dried, filtered and concentrated. Purification by flash chromatography on silica gel (1:9 EtOAc/hexane as elutant) gave 19D (344 mg, 93%) as a white foam.

Example 19

A solution of 19D (344 mg, 0.7 mmol) in TFA/CH₂Cl₂ (1/4) was stirred for 2 h and then concentrated. The residue was lyophilized to give the title compound as a off-white solid (350 mg, 99%). MS (M+H) is 415; HPLC retention time 3.71 min.

Example 20

(R)2-Amino-N-{2-benzyloxy-1-[5-(4-chloro-phenyl)-[1,3,4]oxadiazol-2-yl]-ethyl}-2-methyl-propionamide

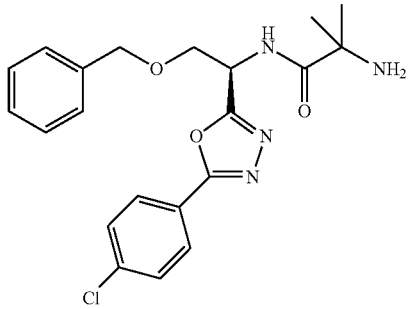

Example 20 was synthesized utilizing the procedures described in Example 19 by using the appropriate starting materials. MS (M+H) is 415; HPLC retention time 3.71 min.

Example 21

(R)2-Amino-N-{2-benzyloxy-1-[5-(2-chloro-phenyl)-[1,3,4]oxadiazol-2-yl]-ethyl}-2-methyl-propionamide

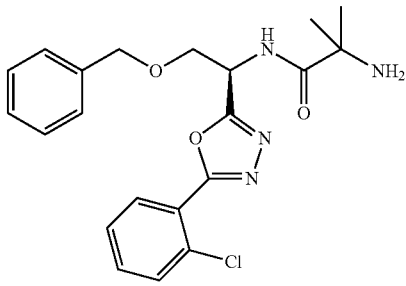

Example 21 was synthesized utilizing the procedures described in Example 19 by using the appropriate starting materials. MS (M+H) is 415; HPLC retention time 3.47 min.

Examples 22 to 28

Examples 22 to 28 were prepared in a manner analogous to that of compounds described previously in the invention and by methods known in the art.

| Example No. | Structure | M + H positive ions |
|---|---|---|
| 22 | 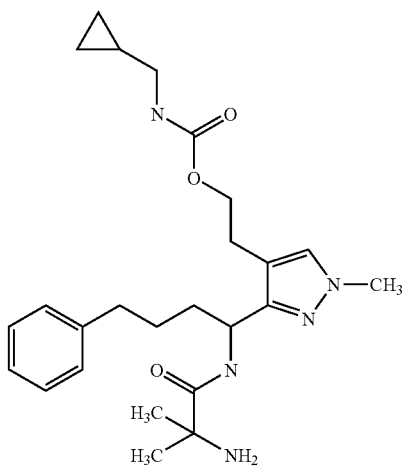 | 456 |
| 23 | 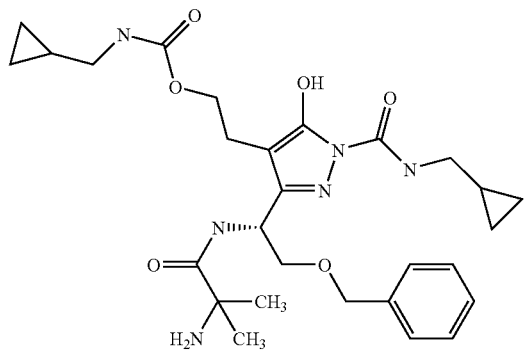 | 557 |

-continued

| Example No. | Structure | M + H positive ions |
|---|---|---|
| 24 | Chiral | 460 |
| 25 | Chiral | 461 |
| 26 | Chiral | 463 |
| 27 | Chiral | 463 |
| 28 | 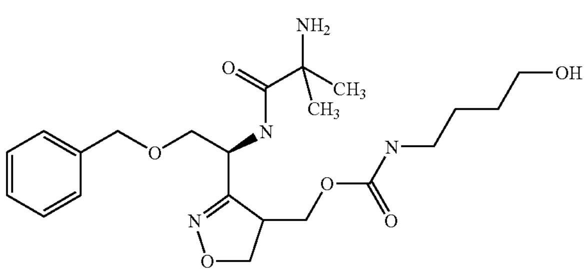 | 451 |

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to Formula I:

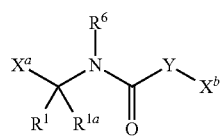

or a stereoisomer or pharmaceutically acceptable salt form thereof, wherein:

$R^1$ and $R^{1a}$ are independently selected from the group consisting of hydrogen, alkyl and arylalkyl;

$X^a$ is selected from the group consisting of

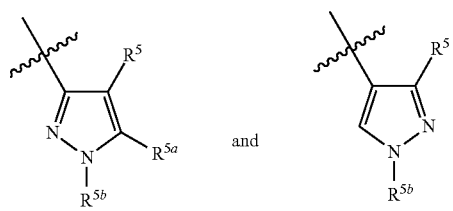

$R^5$ is selected from the group consisting of hydrogen and $J^1$, $R^{5a}$ is selected from the group consisting of hydrogen and aryl, $R^{5b}$ is hydrogen;

$J^1$ is —$(CH_2)_v OC(O)N(T^{1a})T^1$;

$T^1$ and $T^{1a}$ are independently selected from the group consisting of hydrogen, alkyl, alkenyl, alkynyl, lower alkylthioalkyl, alkoxyalkyl, aryl, arylalkyl, heteroaryl, heteroarylalkyl, cycloheteroalkyl and cycloalkyl, wherein alkyl, alkenyl, alkynyl, lower alkylthioalkyl, alkoxyalkyl, aryl, arylalkyl, heteroaryl, heteroarylalkyl, cycloheteroalkyl and cycloalkyl of which may optionally be substituted with 0-3 substituents selected from the group consisting of halogen, hydroxyl, —$NR^{8d}C(O)NR^{8e}R^{8h}$, —$C(O)NR^{8d}R^{8e}$, —$NR^{8d}C(O)R^{8e}$, —CN, —$N(R^{8d})SO_2R^{8e}$, —$OC(O)R^{8d}$, —$SO_2NR^{8d}R^{8e}$, —$SOR^{8h}$, —$SO_2R^{8j}$, alkoxy, —COOH, cycloheteroalkyl and —$C(O)OR^{8k}$, or $T^1$ and $T^{1a}$ may be taken together to form a 3-8 membered heteroaryl or heterocyclo ring;

Y is

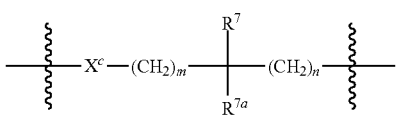

$X^c$ is a direct bond;

$R^7$ and $R^{7a}$ are independently selected from the group consisting of H and alkyl, or $R^7$ and $R^{7a}$ may be taken together to form a 3-7 membered ring;

$R^6$ is hydrogen;

$R^{8d}R^{8e}$, $R^{8h}$, $R^{8j}$ and $R^{8k}$ are independently selected from the group consisting of hydrogen, alkyl, alkenyl, cycloalkyl and aryl;

$X^b$ is —$NR^9R^{10}$;

$R^9$ and $R^{10}$ are each hydrogen m and n are independently 0 to 3; and v is 0 to 5.

2. The compound according to claim 1, wherein:

Y is

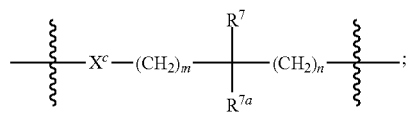

$X^c$ is a direct bond;

$R^7$ and $R^{7a}$ are alkyl;

$R^9$ and $R^{10}$ are hydrogen; and m and n are 0.

3. The compound according to claim 2, wherein:

$R^1$ is alkyl and $R^{1a}$ is hydrogen.

4. The compound according to claim 1 wherein $X^a$ is

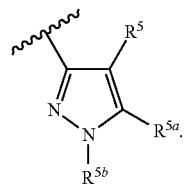

5. The compound according to claim 1, wherein the compound is (S)-2-(3-(1-(2-amino-2-methylpropanamido)-4-phenylbutyl)-1H-pyrazol-4-yl)ethyl 4-hydroxybutylcarbamate.

6. A pharmaceutical composition comprising a compound as defined in claim 1 and a pharmaceutically acceptable carrier or diluent.

7. The pharmaceutical composition of claim 6 further comprising at least one additional compound selected from the group consisting of parathyroid hormone, bisphosphonates, estrogen, testosterone, selective estrogen receptor modulators, selective androgen receptor modulators, progestin receptor agonists, anti-diabetic agents, anti-hypertensive agents, anti-inflammatory agents, anti-osteoporosis agents, anti-obesity agents, cardiac glycosides, cholesterol lowering agents and thyroid mimetics.

8. The pharmaceutical composition of claim 6 further comprising at least one nutritional supplement.

9. A pharmaceutical composition comprising a compound as defined in claim 5 and a pharmaceutically acceptable carrier or diluent.

10. The pharmaceutical composition of claim 9 further comprising at least one additional compound selected from the group consisting of parathyroid hormone, bisphosphonates, estrogen, testosterone, selective estrogen receptor modulators, selective androgen receptor modulators, progestin receptor agonists, anti-diabetic agents, anti-hypertensive agents, anti-inflammatory agents, anti-osteoporosis agents, anti-obesity agents, cardiac glycosides, cholesterol lowering agents and thyroid mimetics.

11. The pharmaceutical composition of claim 9 further comprising at least one nutritional supplement.

* * * * *

UNITED STATES PATENT AND TRADEMARK OFFICE
CERTIFICATE OF CORRECTION

PATENT NO. : 8,143,425 B2  Page 1 of 1
APPLICATION NO. : 11/247491
DATED : March 27, 2012
INVENTOR(S) : William R. Ewing et al.

It is certified that error appears in the above-identified patent and that said Letters Patent is hereby corrected as shown below:

On the Title Page:

Item (56), References Cited, under OTHER PUBLICATIONS:
    Hamann. L. et al. reference, change "pyridono[5,6-9]quinoline" to
-- pyridono[5,6-g]quinoline --.

The reference should read:

-- Hamann. L. et al., "Discovery of a Potent, Orally Active, Nonsteroidal Androgen receptor Agonist: 4-Ethyl-1,2,3,4-tetrahydro-6-(trifluoromethyl)-8-pyridono[5,6-g]quinoline (LG121071)", J. Med. Chem., vol. 42, pp. 210-212 (1999). --.

In the Claims:

Column 69, Claim 1, line 65, change "$R^{8d}R^{8e}$" to -- $R^{8d}, R^{8e}$ --.

Signed and Sealed this
Twenty-fifth Day of September, 2012

David J. Kappos
*Director of the United States Patent and Trademark Office*